United States Patent
Kim et al.

(10) Patent No.: US 10,083,520 B2
(45) Date of Patent: Sep. 25, 2018

(54) RADIOGRAPHIC IMAGING APPARATUS AND RADIOGRAPHIC IMAGE GENERATION METHOD

(71) Applicant: SAMSUNG ELECTRONICS CO., LTD., Suwon-si (KR)

(72) Inventors: Sung Su Kim, Yongin-si (KR); Hyun Hwa Oh, Hwaseong-si (KR); Dong Goo Kang, Hwaseong-si (KR); Young Hun Sung, Hwaseong-si (KR); Kang Eui Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 482 days.

(21) Appl. No.: 14/295,943

(22) Filed: Jun. 4, 2014

(65) Prior Publication Data

US 2014/0355739 A1 Dec. 4, 2014

(30) Foreign Application Priority Data

Jun. 4, 2013 (KR) ........................ 10-2013-0064218

(51) Int. Cl.
*G06T 7/33* (2017.01)
*G06T 5/50* (2006.01)
(Continued)

(52) U.S. Cl.
CPC ............ *G06T 7/337* (2017.01); *A61B 6/5235* (2013.01); *G06K 9/3208* (2013.01);
(Continued)

(58) Field of Classification Search
CPC .... A61B 6/00; A61B 6/42; A61B 6/46; A61B 6/461; A61B 6/463; A61B 6/466; A61B 6/52; A61B 6/5211; A61B 6/5229; A61B 6/5235; A61B 6/5258; G06T 5/00; G06T 5/006; G06T 5/50; G06T 7/00; G06T 7/0002; G06T 7/0012; G06T 7/0014; G06T 7/30; G06T 7/32; G06T 7/33;
(Continued)

(56) References Cited

U.S. PATENT DOCUMENTS

2004/0081280 A1* 4/2004 Avinash ................. A61B 6/405
378/98.9
2004/0252873 A1* 12/2004 Avinash ................. A61B 6/032
382/132
(Continued)

FOREIGN PATENT DOCUMENTS

JP 2010-5016 A 1/2010
KR 10-0702240 B1 4/2007

*Primary Examiner* — Anastasia Midkiff
(74) *Attorney, Agent, or Firm* — Sughrue Mion, PLLC

(57) ABSTRACT

The radiographic image generation method includes acquiring a plurality of radiographic images corresponding to a number of radiation dose portions by emitting radiation to an object by dividing a radiation exposure dose into the radiation dose portions, and by detecting the emitted radiation, and matching the plurality of acquired radiographic images, by shifting all or a portion of data of a plurality of the acquired radiographic images such that the corresponding articles within a plurality of the acquired radiographic images are positioned at a same relative position in each of the acquired radiographic images.

18 Claims, 20 Drawing Sheets

(51) Int. Cl.

| | | |
|---|---|---|
| *G06K 9/32* | (2006.01) | |
| *G06K 9/62* | (2006.01) | |
| *A61B 6/00* | (2006.01) | |
| *G06K 9/78* | (2006.01) | |
| *G06T 7/73* | (2017.01) | |
| *G01N 23/04* | (2018.01) | |
| *G06K 9/20* | (2006.01) | |
| *G06T 5/00* | (2006.01) | |
| *G06T 7/00* | (2017.01) | |

(52) U.S. Cl.
CPC .............. *G06K 9/6203* (2013.01); *G06K 9/78* (2013.01); *G06T 5/50* (2013.01); *G06T 7/33* (2017.01); *G06T 7/74* (2017.01); *G06T 7/97* (2017.01); *G01N 23/04* (2013.01); *G06K 2009/2045* (2013.01); *G06K 2009/6213* (2013.01); *G06T 5/006* (2013.01); *G06T 7/0014* (2013.01); *G06T 2207/20212* (2013.01); *G06T 2207/20221* (2013.01); *G06T 2207/20228* (2013.01); *G06T 2219/2004* (2013.01); *G06T 2219/2016* (2013.01)

(58) Field of Classification Search
CPC .. G06T 7/337; G06T 7/37; G06T 7/60; G06T 7/70; G06T 7/07; G06T 7/74; G06T 7/97; G06T 2210/41; G06T 2211/00; G06T 2211/40; G06T 2215/00; G06T 2207/00; G06T 2207/10; G06T 2207/10072; G06T 2207/10081; G06T 2207/10116; G06T 2207/20; G06T 2207/20212; G06T 2207/20221; G06T 2207/20228; G06T 2207/30; G06T 2207/30004; G06T 2219/00; G06T 2219/20; G06T 2219/2004; G06T 2219/2016; G06K 9/20; G06K 9/2054; G06K 9/32; G06K 9/3208; G06K 9/3216; G06K 9/3233; G06K 9/3241; G06K 9/3275; G06K 9/60; G06K 9/62; G06K 9/6201–9/6203; G06K 9/6212; G06K 9/6215; G06K 9/6288; G06K 9/6289; G06K 9/64; G06K 9/68; G06K 9/78; G06K 9/80; G06K 2009/2045; G06K 2009/3291; G06K 2009/6213

See application file for complete search history.

(56) References Cited

U.S. PATENT DOCUMENTS

| | | | |
|---|---|---|---|
| 2006/0257051 A1* | 11/2006 | Zavadsky | G06T 3/4038 |
| | | | 382/294 |
| 2007/0189436 A1 | 8/2007 | Goto et al. | |
| 2008/0112649 A1 | 5/2008 | Chen et al. | |
| 2008/0298539 A1 | 12/2008 | Nakanishi | |
| 2013/0121537 A1* | 5/2013 | Monobe | H04N 5/23254 |
| | | | 382/106 |

* cited by examiner

RADIOGRAPHIC IMAGING APPARATUS AND RADIOGRAPHIC IMAGE GENERATION METHOD

CROSS-REFERENCE TO RELATED APPLICATION

This application claims priority from Korean Patent Application No. 10-2013-0064218, filed on Jun. 4, 2013 in the Korean Intellectual Property Office, the disclosure of which is incorporated herein by reference in its entirety.

BACKGROUND

1. Field

Apparatuses and methods consistent with exemplary embodiments relate to a radiographic imaging apparatus and a radiographic image generation method.

2. Description of the Related Art

In general, a radiographic imaging apparatus acquires an image of the internal areas of an object, such as a human body or an article, using radiation, for example, X-rays, based on properties in that, when radiation is applied to an object, the radiation is absorbed or transmitted by the object according to characteristics of a material through which radiation passes. Since the radiographic imaging apparatus may easily detect the structure of an object, it may be used to detect lesions within a human body in medicine, or to detect the internal structure of an article or a machine part. Further, the radiographic imaging apparatus may be used to check the baggage in an airport, etc.

Radiographic imaging apparatuses include, for example, a digital radiography (DR) apparatus, a computed tomography (CT) apparatus, and a full field digital mammography (FFDM) apparatus.

Specifically, the radiographic imaging apparatus generates a radiographic image by emitting radiation to an object, receiving radiation having passed through the object or directly having reached the radiographic imaging apparatus, and converting the received radiation into electrical signals. The image is generated based on the converted electrical signals and is displayed, so that the user may observe the structures of the object.

SUMMARY

One or more exemplary embodiments provide a radiographic imaging apparatus and a radiographic image generation method which may acquire a plurality of radiographic images in which noise or artifacts according to movement of an object are removed or minimized.

One or more exemplary embodiments provide a radiographic imaging apparatus and a radiographic image generation method which may prevent shaking of a plurality of radiographic images or difference among the plurality of radiographic images due to movement of an object.

In accordance with an aspect of an exemplary embodiment, a radiographic image generation method includes acquiring a plurality of radiographic images corresponding to the number of radiation dose portions by emitting radiation to an object by dividing a radiation exposure dose, and by detecting the emitted radiation, and matching the plurality of acquired radiographic images. In this case, the radiographic image generation method may further include combining the plurality of matched radiographic images. Further, in the radiographic image generation method, a multi-energy radiographic image may be generated by acquiring a plurality of matched radiographic images of different energies by emitting radiation of different energies to the object and combining the plurality of matched radiographic images acquired based on emission of radiation of different energies.

In accordance with an aspect of an exemplary embodiment, a radiographic imaging apparatus includes a radiation source emitting radiation to an object by dividing a radiation exposure dose required to acquire a radiographic image, the radiation being emitted to the object the number of times corresponding to the number of divided radiation dose portions, a radiation detector receiving the radiation emitted from the radiation source, converting the received radiation into electrical signals, and then outputting the electrical signals, and an image processor acquiring a plurality of radiographic images corresponding to the number of divided radiation dose portions by reading out the electrical signals, and matching the plurality of acquired radiographic images.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
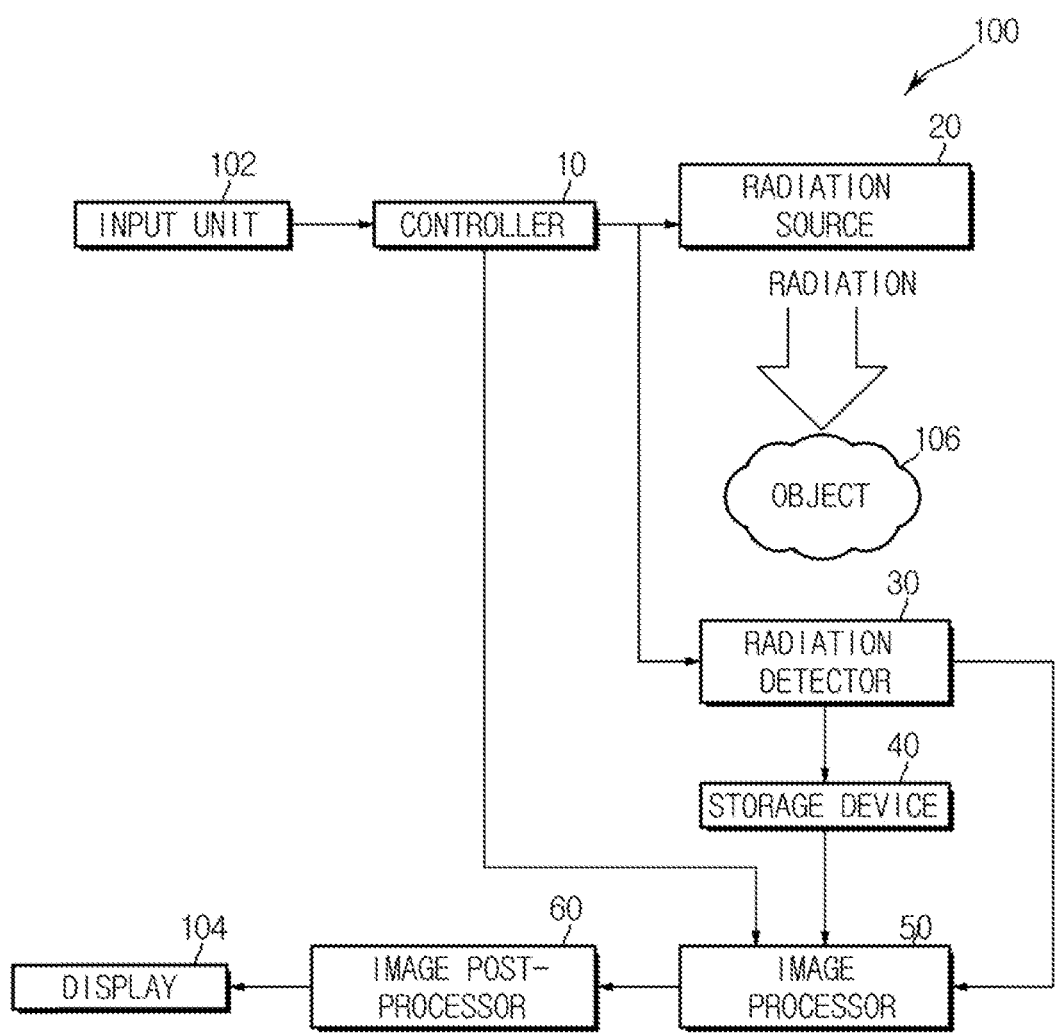
FIG. 1 is a view illustrating the configuration of a radiographic imaging apparatus in accordance with an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a view illustrating the configuration of a radiographic imaging apparatus 100 in accordance with an exemplary embodiment.

As exemplarily shown in FIG. 1, a radiographic imaging apparatus in accordance with an exemplary embodiment may include an input unit 102, a controller 10, a radiation source 20, a radiation detector 30, a storage device 40, an image processor 50, and a display 104.

The input unit 102 may receive various instructions, commands, or information to control the radiographic imaging apparatus, input by a user. Here, the various instructions or commands may include various instructions or commands regarding radiography or radiographic image processing. Further, the various information include information regarding the number of times of irradiation, the number of radiation exposure dose portions, a radiation exposure dose at each irradiation, or the overall radiation exposure dose.

The input unit 102 may include, for example, various buttons, a keyboard, a mouse, a track-ball, a track-pad, a touchscreen panel, various levers, a handle, or a stick.

The input unit 102 may be installed directly in the radiographic imaging apparatus, or may be provided on a separate workstation which may transmit and receive data through a wired/wireless network.

The various instructions, commands or information input through the input unit 102 may be transmitted to the controller 10.

The controller 10 may generate a designated control command and transmit the generated control command to the radiation source 20, the radiation detector 30, or the image processor 50, thus controlling the overall operation of the radiographic imaging apparatus including the radiation source 20, etc.

The controller 10 may receive the user instructions or command or the various pieces of information input through the input unit 102 and control a designated operation of the radiographic imaging apparatus using the received instructions, command, or information. Further, the controller 10 may control a designated operation of the radiographic imaging apparatus according to predefined system settings.

The controller 10 may receive a radiography start command or a radiography standby command from the input unit 102, and start or stand by radiography by generating operation start or standby command to the radiation source 20 or the radiation detector 30 according to the received radiography start command.

The controller 10 may control operation of the radiation source 20. As examples of the operation of the radiation source 20 controlled by the controller 10, there may be irradiation direction adjustment, position movement, and adjustment of voltage applied to start irradiation or to irradiate. For example, the controller 10 may generate a designated control signal, and transmit the generated control signal to the radiation source 20 so that the radiation source 20 may apply power of designated voltage to a radiation tube according to the control signal of the controller 10 so as to generate radiation of designated energy. In this case, the energy of the generated radiation may be determined according to the applied voltage. Furthermore, the controller 10 may also control operations of a designated collimator or various filters as needed.

The controller 10 may control the radiation source 20 so as to emit radiation to an object 106 at a designated divided radiation exposure dose designated number of irradiation times. The designated divided radiation exposure dose is acquired by dividing a radiation exposure dose to acquire a radiographic image by a designated number of divided radiation dose portions. The number of divided radiation dose portions may be equal to a designated number of times of irradiation. In accordance with exemplary embodiments, the number of divided radiation dose portions and the radiation exposure dose when irradiation occurs once may be determined by the user instructions or command input through the input unit 102, or be determined according to predefined settings, etc.

Further, the controller 10 may control various operations regarding the radiation detector 30, such as movement of the radiation detector 30, readout of acquired radiographic signals, and reset of the radiation detector 30.

For example, the controller 10 may generate a control command to move the radiation detector 30 so as to properly receive radiation according to movement of the radiation source 20, and generate a control command to cause the image processor 50 to read out a radiographic signal stored in the radiation detector 30. Furthermore, the controller 10 may transmit the radiographic signal stored in the radiation detector 30 to the storage device 40 so that the storage device 40 may temporarily or non-temporarily store the radiographic signal.

The controller 10 may control the radiation source 20 and the radiation detector 30 so as to operate together. When the radiation source 20 emits radiation to the object 106, the radiation detector 30 receives radiation transmitted by the object 106, converts the radiation into an electrical signal, i.e., a radiographic signal, and then stores the radiographic signal. In this case, the radiographic signal converted from the received radiation may be stored in a capacitor of the radiation detector 30 one time or temporarily. Therefore, if a new radiographic signal is generated according to new radiation, the existing radiographic signal stored in the capacitor may be deleted or influence the new radiographic signal and thus cause noise on a radiographic image. Therefore, the controller 10 may generate a designated control command regarding the radiation source 20 and the radiation detector 30 so that the radiation source 20 and the radiation detector 30 may be synchronized and be operated together, and transmit the generated control command to the radiation source 20 and the radiation detector 30 so as to adjust synchronization between irradiation and detection of radiation.

The controller 10 may cause the radiation detector 30 to transmit the existing radiographic signal to a different storage space, for example, to the storage device 40, or cause the image processor 50 to read out the existing radiographic signal, before the radiation source 20 emits radiation, so that the radiation detector 30 may prepare radiation reception, i.e., be reset, before irradiation.

Specifically, before the radiation source 20 emits radiation in the direction of the object 106, the controller 10 may generate a designated control command, i.e., a reset command, regarding the radiation detector 30 so as to acquire a proper radiographic signal according to the emitted radiation, and transmit the generated reset command to the radiation detector 30 or the image processor 50 to reset the radiation detector 30. For example, the controller 10 may generate a designated control command to transmit the existing radiographic signal stored in the radiation detector 30 to a different storage space, for example, to the storage device 40, so that the existing radiographic signal may be stored in the storage device 40, or to reset the radiation detector 30 while causing the image processor 50 to read out the existing radiographic signal stored in the radiation detector 30 before irradiation, and transmit the control command to the radiation detector 30 or the image processor 50.

The controller 10 may be one of various processors including at least one chip provided with an integrated circuit, and such a central processor may be provided within the radiographic imaging apparatus or be provided on an external workstation.

Hereinafter, the radiation source 20 will be described.

Figure 2:
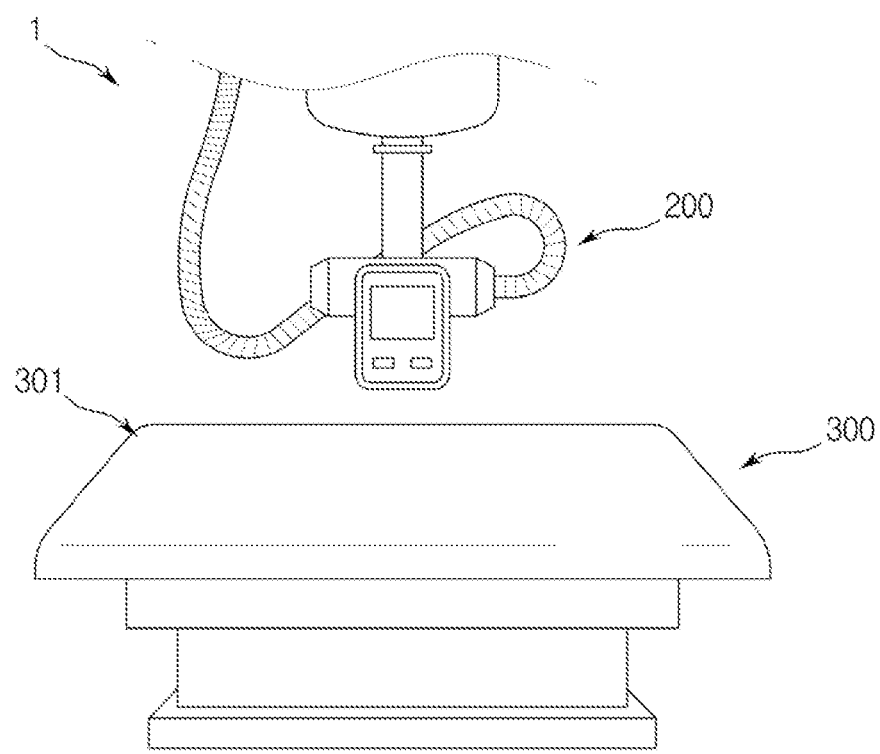
FIG. 2 is a front view illustrating the radiographic imaging apparatus in accordance with an exemplary embodiment.

FIG. 2 is a front view illustrating the radiographic imaging apparatus in accordance with an exemplary embodiment. In accordance with an exemplary embodiment, the radiographic imaging apparatus may be a digital radiography (DR) apparatus 1, as exemplarily shown in FIG. 2. Although the digital radiography (DR) apparatus 1 will be described below, the radiographic imaging apparatus may be a mammography apparatus or a computed tomography (CT) apparatus.

In accordance with an exemplary embodiment, the radiation source 20 may be installed on an irradiation module 200 of the digital radiography (DR) apparatus 1. The irradiation module 200 may emit radiation in a designated direction, for example, a direction of the ground surface, such as, for example, a surface 301 of an examination table 300, as exemplarily shown in FIG. 2. Of course, the irradiation module 200 may emit radiation in a direction in parallel with the ground surface.

Figure 3:
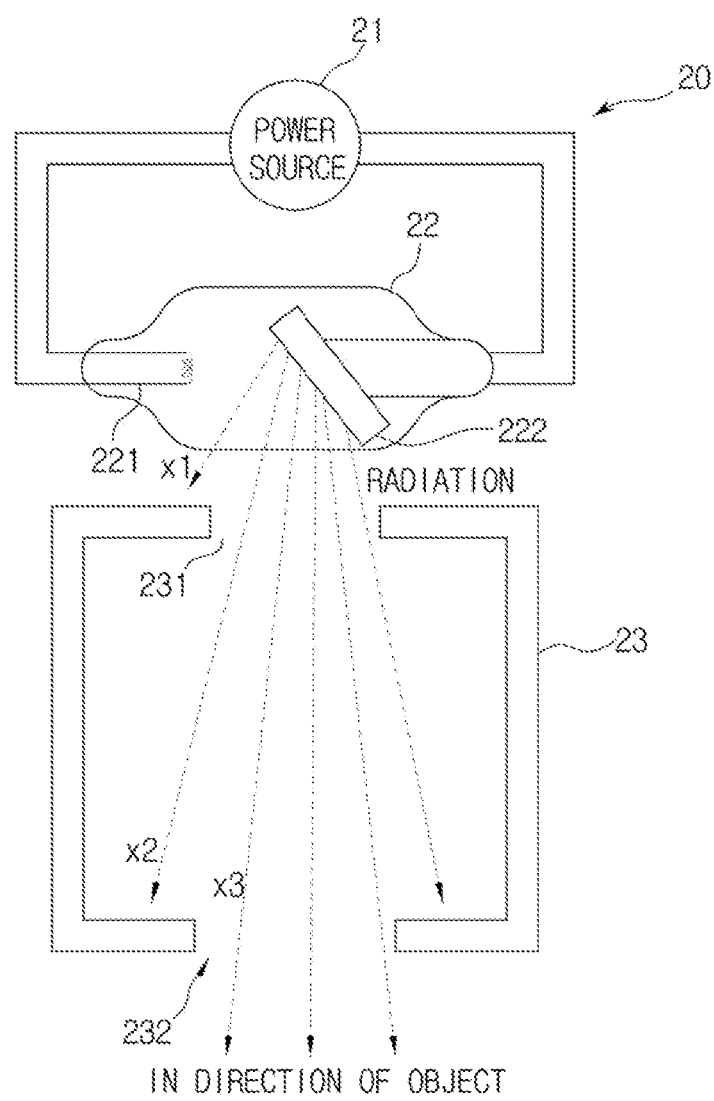
FIG. 3 is a view illustrating the configuration of a radiation source in accordance with an exemplary embodiment.

FIG. 3 is a view illustrating the configuration of a radiation source in accordance with an exemplary embodiment.

As exemplarily shown in FIG. 3, the radiation source 20 may include a power source 21, a radiation tube 22, and a collimator 23 having an input port 231 and an output port 232. In detail, the radiation tube 22 may include a cathode filament 221 and an anode 222.

The power source 21 may apply designated voltage to the radiation tube 22. When the designated voltage is applied from the power source 21 to the radiation tube 22, electrons located on or around the cathode filament 221 in the radiation tube 22 are accelerated and moved in the direction of the anode 222. The accelerated electrons collide with the anode 222 and are rapidly decelerated by Coulomb's force and, at this time, radiation is generated from the anode 222 based on the law of energy conservation. The generated radiation is emitted in a designated direction.

A potential difference between the cathode filament 221 and the anode 222 of the radiation tube 22 is referred to as tube voltage, and current flowing by the electrons colliding with the anode 22 is referred to as tube current. As tube voltage increases, the velocity of electrons increases and thus, energy of generated radiation increases. As tube current increases, a radiation dose may increase.

The collimator 23 may transmit radiation in specific directions, for example, second radiation x2 and third radiation x3, and filter out radiation progressing in directions other than the specific directions, for example, first radiation x1, through absorption or reflection, so that radiation may be emitted within a designated range and in a designated direction. The collimator 23 may be installed on an irradiation path, as exemplarily shown in FIG. 3. A user may control an irradiation direction or an irradiation range with X-rays through the collimator 23.

The radiation source 20 may generate radiation plural times and emit the radiation to an object 106. In this case, the radiation source 20 may emit radiation of the same energy or radiation of different energies whenever the radiation source 20 emits radiation.

For example, in accordance with an exemplary embodiment, the radiation source 20 may generate multi-energy radiation through tube voltage conversion or filter conversion and then emit the generated multi-energy radiation to the object 106. For example, the radiation source 20 may emit radiation of a plurality of different energies to the object 106. Further, the radiation source 20 may emit radiation while varying the irradiation time of each radiation.

Further, the radiation source 20 may divide a radiation exposure dose into radiation dose portions to acquire a radiographic image and emit radiation to the object 106 a number of times corresponding to the number of radiation dose portions. In this case, the exposure dose of emitted radiation may be determined by the divided radiation exposure dose portions. Further, the number of times of irradiation may be determined by the number of radiation dose portions.

Hereinafter, division of a radiation exposure dose and irradiation of the radiation source 20 thereby will be described.

FIGS. 4 to 8 are graphs illustrating whether or not the radiation source 20 is operated. In the graphs of FIGS. 4 to 8, the x-axis means time. In the graphs, a protruding portion means that radiation is emitted, and other portions mean that emission of radiation is stopped. A mark above the protruding portion denotes an identification number to identify emitted radiation. In the graphs, the respective identification numbers are defined by an energy spectrum and an emission sequence of radiation emitted by the radiation source 20. For example, identification numbers having the same first digit, for example, E11 and E12, mean radiation of the same energy spectrum. On the other hand, identification numbers having different first digits, for example, E11 and E21, mean radiation of different energy spectrums. In the graphs, t positioned below the protruding portion means an irradiation time with radiation. Therefore, as the protruding portion becomes longer, a radiation exposure duration increases.

Figure 4:
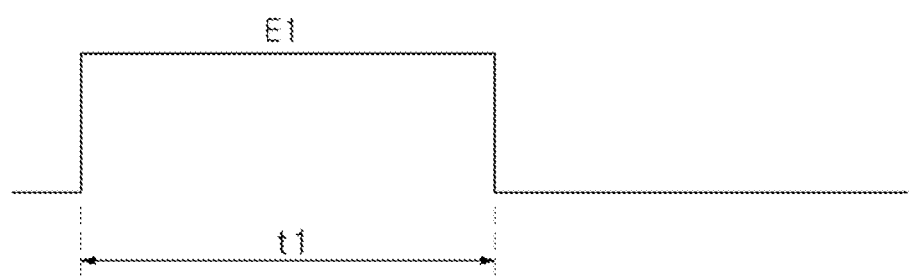
FIGS. 4, 5, 6, 7, and 8 are graphs illustrating examples of division of a radiation exposure dose.
Figure 5:
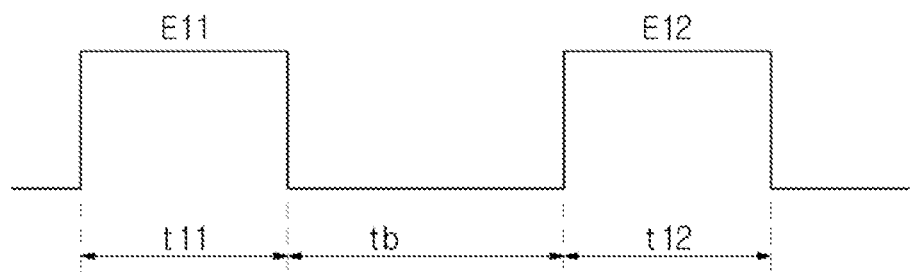

FIGS. 4 and 5 are graphs illustrating examples of a radiation exposure dose.

As exemplarily shown in FIG. 4, it is assumed that radiation E1 of a first exposure dose is generally required to acquire a designated radiographic image through the radiation source 20. In this case, the radiation of a total of the first exposure dose may be emitted to the object 106 by emitting the first radiation E1 for a designated first time t1, for example, 1 second, to the object 106.

In accordance with an exemplary embodiment, the radiation source 20 may divide a radiation exposure dose to be emitted, i.e., the first exposure dose E1, into a plural number and then emit a divided exposure dose plural times, as exemplarily shown in FIG. 5. Here, the number of the radiation dose portions and the number of times of irradiation may be the same. That is, the sum of an exposure dose of eleventh radiation E11 (an eleventh exposure dose) and an exposure dose of twelfth radiation E12 (a twelfth exposure dose) shown in FIG. 5 may be equal to the first exposure dose of the first radiation E1 shown in FIG. 4. In the same manner, the sum of an irradiation time t11 of the eleventh radiation E1 and an irradiation time t12 of the twelfth radiation E12 shown in FIG. 5 may be equal to the irradiation time t1 of the first radiation E1 shown in FIG. 4. The number of the divided radiation exposure dose portions and the number of times of irradiation may be predetermined by a user or a system designer.

The exposure doses of radiation whenever radiation is emitted, i.e., the exposure dose of eleventh radiation E11 and the exposure dose of twelfth radiation E12 may be the same, or be different. In this case, the irradiation time t11 of the eleventh radiation E11 and the irradiation time t12 of the twelfth radiation E12 may be the same, or be different. Such irradiation times may be predetermined by the user or the system designer.

Further, in this case, irradiation may be performed at a designated time interval tb, as exemplarily shown in FIG. 5. For example, emission of the twelfth radiation E12 may be started after the designated time tb from termination of emission of the eleventh radiation E11 has elapsed. Such a time interval tb may be predetermined by the user or the system designer.

Although the radiation exposure dose is divided and radiation is emitted to the object 106 plural times according to the divided radiation exposure dose, as exemplarily shown in FIG. 5, the overall radiation exposure dose of this case may be equal to that of the case in which radiation is emitted without division of the total radiation exposure dose, as exemplarily shown in FIG. 4.

In accordance with an exemplary embodiment, the radiation source 20 may emit radiation of different energies to the object 106. When radiation of different energies transmitted by the object 106 is detected, a multi-energy image may be acquired. Materials within the object 106 may have different contrasts according to energy bands of radiation. Therefore, if the multi-energy image is acquired by emitting radiation of different energies, the materials within the object 106 may be easily distinguished.

Figure 6:
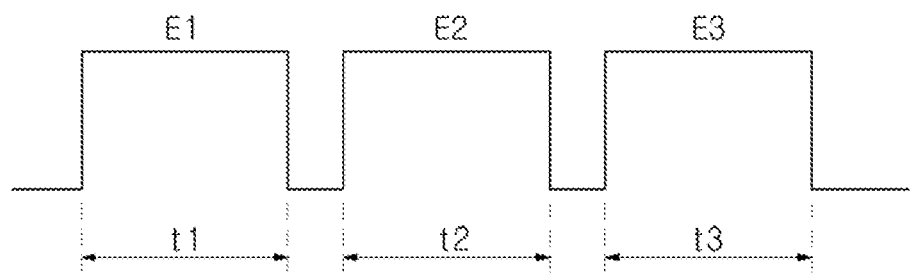
Figure 7:
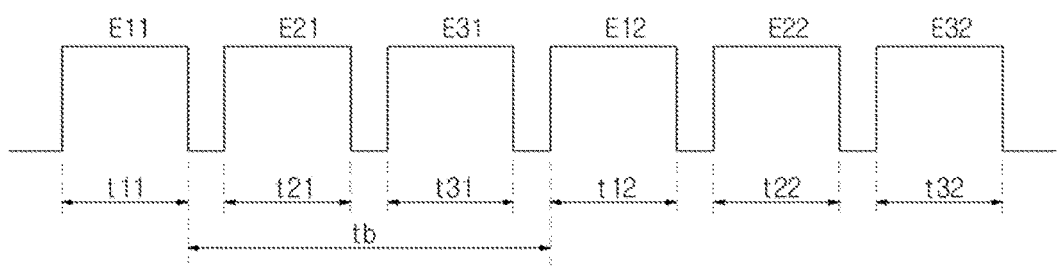

FIGS. 6 and 7 are graphs illustrating examples of a radiation exposure dose if multi-energy radiation is emitted.

It is assumed that, in order to acquire a designated multi-energy radiographic image, radiation of a plurality of energies, for example, first radiation E1 of first energy, second radiation E2 of second energy, and third radiation E3 of third energy, is emitted for designated first time t1, second time t2, and third time t3, as exemplarily shown in FIG. 6. In this case, designated exposure doses, for example, first to third exposure doses, of the first to third radiation E1 to E3 are emitted to the object 106. The respective exposure doses of the first to third radiation E1 to E3 may be the same or be different, or be partially the same and partially different.

In accordance with an exemplary embodiment, the radiation source 20 may divide radiation exposure doses required to acquire radiation, i.e., the first to third exposure doses E1 to E3, into a plural number and then emit radiation at divided exposure doses plural times, as exemplarily shown in FIG. 7. As described above, the number of the divided radiation doses and the number of times of irradiation may be the same. That is, the sum of the exposure dose of eleventh radiation E11 and an exposure dose of twelfth radiation E12 shown in FIG. 7 may be equal to the first exposure dose of the first radiation E1 shown in FIG. 6. In the same manner, the sum of the exposure dose of twenty-first E21 and an exposure dose of twenty-second E12 shown in FIG. 7 may be equal to the second exposure dose of the second radiation E2 shown in FIG. 6. Further, the sum of the exposure dose of thirty-first E31 and an exposure dose of thirty-second E32 shown in FIG. 7 may be equal to the third exposure dose of the third radiation E3 shown in FIG. 6. As described above, the sums of irradiation times t11, t21, and t31 of the eleventh radiation E11 to the thirty-first radiation E31 and irradiation times t12, t22, and t32 of the twelfth radiation E12 to the thirty-second radiation E32 may be equal to the irradiation times t1 to t3 of the first radiation E1 to the third radiation E3.

The exposure doses of radiation whenever radiation is emitted, i.e., the exposure dose of the eleventh radiation E11 and the exposure dose of the twelfth radiation E12 may be the same, or be different. In the same manner, the exposure dose of the twenty-first radiation E21 or the exposure dose of the thirty-first radiation E31 and the exposure dose of the twenty-second radiation E22 or the exposure dose of the thirty-second radiation E32 may be the same, or be different. Further, the exposure doses of the eleventh radiation E11 to the thirty-second radiation E32 may be the same or be different, or be partially the same and partially different.

In accordance with an exemplary embodiment, the radiation source 20 may emit radiation of different energies, for example, the eleventh radiation E11 to the thirty-first radiation E31, according to a designated pattern. For example, the radiation source 20 may sequentially and repeatedly emit radiation of different energies, as exemplarily shown in FIG. 7. Specifically, the radiation source 20 may sequentially emit the eleventh radiation E11 to the thirty-first radiation E31 by first emitting the eleventh radiation E11 to the object 106, emitting the twenty-first radiation E21 to the object 106 just after emission of the eleventh radiation E11 has been completed or after a designated time from emission of the eleventh radiation E11 has elapsed, and emitting the thirty-first radiation E31 to the object 106 just after emission of the twenty-first radiation E21 has been completed or after a designated time from emission of the twenty-first radiation E21 has elapsed. Further, the radiation source 20 may sequentially emit radiation of different energies to the object 106 by emitting the twelfth radiation E12 just after emission of the thirty-first radiation E31 has been completed or after a designated time from emission of the thirty-first radiation E31 has elapsed. In this case, radiation of the same energy, for example, the eleventh radiation E11 and the twelfth radiation E12, may be emitted at the designated time interval tb, as exemplarily shown in FIG. 7.

As described above, since the exposure doses of the radiation of plural energies emitted to the object 106, i.e., the radiation E11 to the radiation E32, are acquired by dividing radiation exposure doses to be originally emitted, as exemplarily shown in FIGS. 6 and 7, the overall radiation exposure dose of this case may be equal to that of the case in which radiation is emitted without division of the total radiation exposure dose, as exemplarily shown in FIG. 6. That is, the radiation exposure doses to the object 106 in the cases of FIGS. 6 and 7 may be the same.

Figure 8:
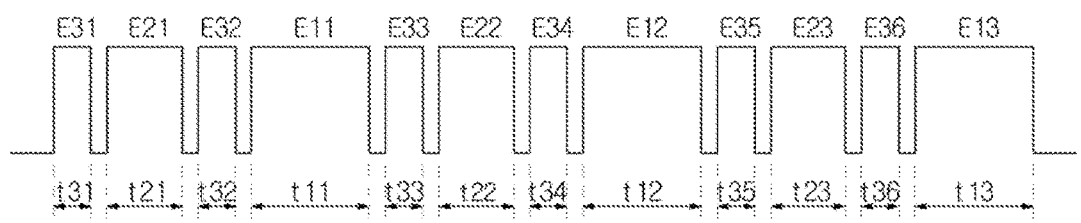

FIG. 8 is a graph illustrating one example of division of a radiation exposure dose in case of irradiation with multi-energy radiation.

The radiation exposure doses of the radiation of different energies, i.e., the radiation E1 to the radiation E3, shown in FIG. 6 may be divided into different numbers, as exemplarily shown in FIG. 8. For example, the exposure dose of the first radiation E1 of first energy and the exposure dose of the second radiation E2 of second energy may be respectively divided into three dose portions, respectively, and the exposure dose of the third radiation E3 of third energy may be divided into six dose portions. Thereby, while the first radiation E1 of first energy and the second radiation E2 of second energy are respectively emitted three times, the third radiation E3 of third energy may be emitted five times. In this case, the irradiation times t11, t21, and t31 of the radiation E1 to the radiation E3 of different energies may be different. Therefore, irradiation intervals of the radiation of the same energy may be different.

Further, in terms of the pattern of radiation, the eleventh radiation E11 to the thirty-first radiation E31 are not sequentially emitted, differing from FIG. 7. For example, as exemplarily shown in FIG. 8, the thirty-first radiation E31 based on the third radiation E3 may be emitted, the twenty-first radiation E21 based on the second radiation E2 may be emitted, the thirty-second radiation E32 based on the third radiation E3 may be emitted, and then, the eleventh radiation E11 based on the first radiation E1 may be emitted.

If a radiation exposure dose to be emitted to the object 106 to acquire a radiographic image is divided and radiation is emitted to the object 106 a designated number of times, for example, the number of divided radiation dose portions is emitted at designated time intervals, as described above, a plurality of radiographic images may be acquired at corresponding time intervals. If radiation of multi-energies is divided, as exemplarily shown in FIGS. 7 and 8, a plurality of multi-energy radiographic images may be acquired.

Hereinafter, the radiation detector 30 will be described.

The radiation detector 30 receives radiation emitted from the radiation source 20 and converts the received radiation into an electrical signal, i.e., a radiographic signal. Some of the received radiation may be radiation which is attenuated according to a designated attenuation rate while passing through the object 106.

Figure 9:
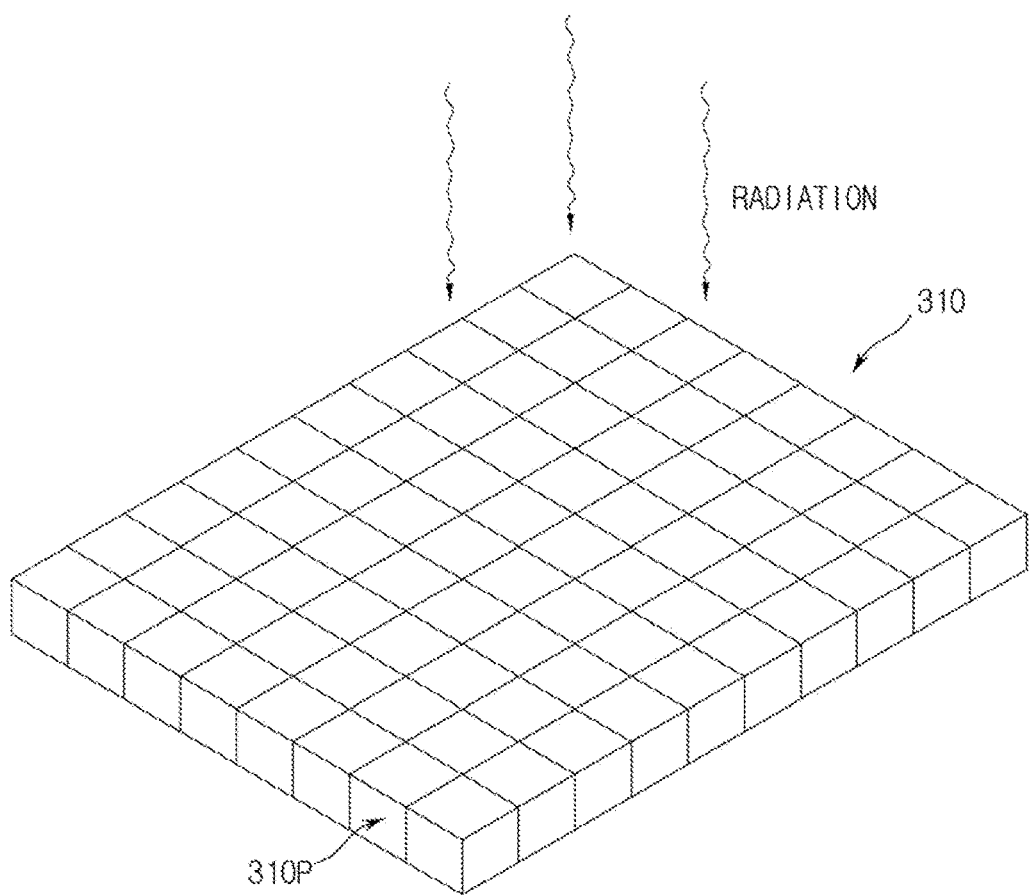
FIG. 9 is a view of a radiation detection panel in accordance with an exemplary embodiment.

FIG. 9 is a view of a radiation detection panel in accordance with an exemplary embodiment.

The radiation detector 30 may include a radiation detection panel 310 divided into a plurality of pixels 310p to receive radiation emitted from the radiation source 20, as exemplarily shown in FIG. 9. When radiation reaches the pixels 310p, the respective pixels 310p of the radiation detection panel 310 output visible light photons corresponding to the radiation, senses the visible light photons, and generate an electrical signal corresponding to the sensed visible light photons, thus converting the radiation into a radiation signal corresponding to the radiation.

Figure 10:
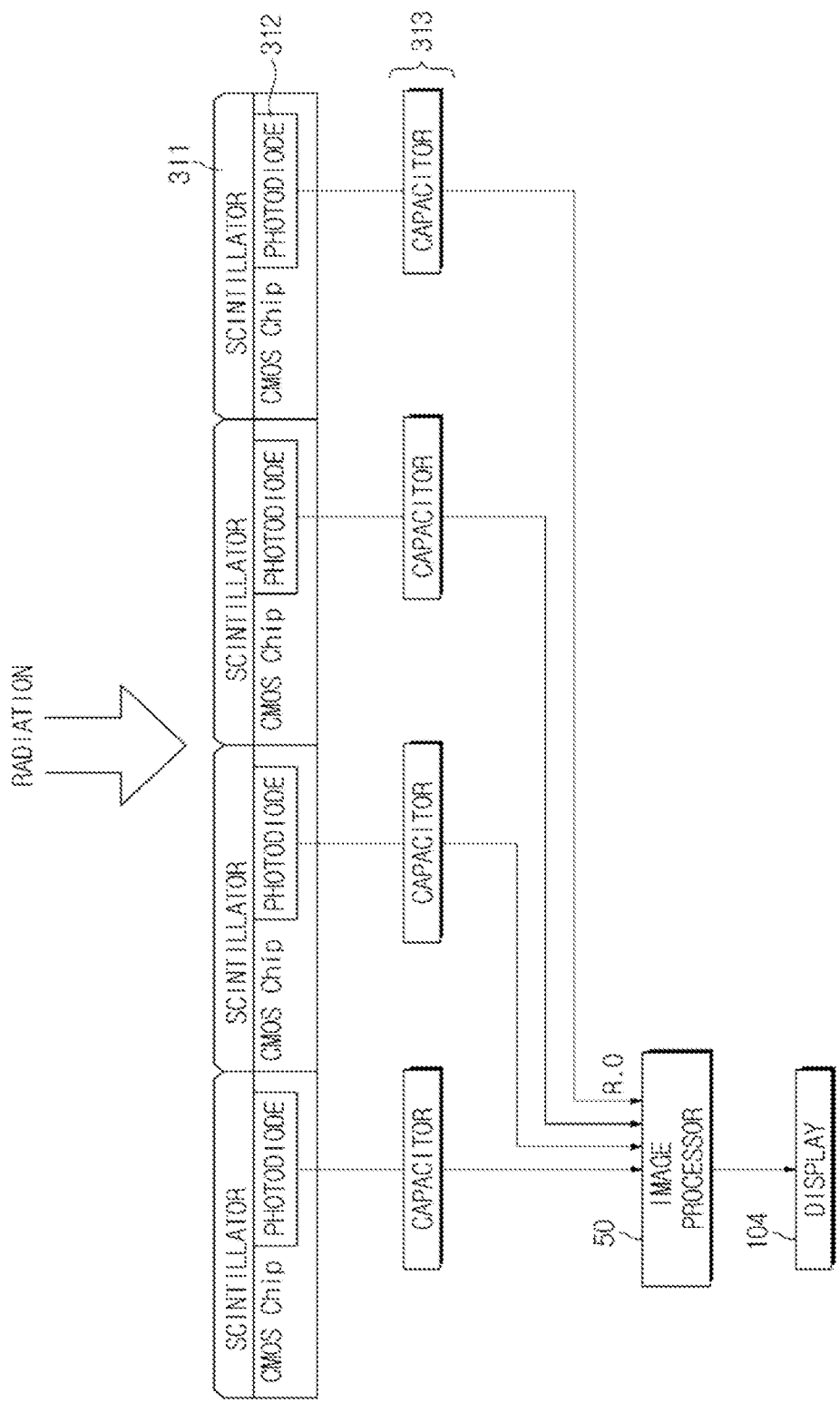
FIGS. 10, 11, and 12 are views of radiation detector in accordance with an exemplary embodiment.
Figure 11:
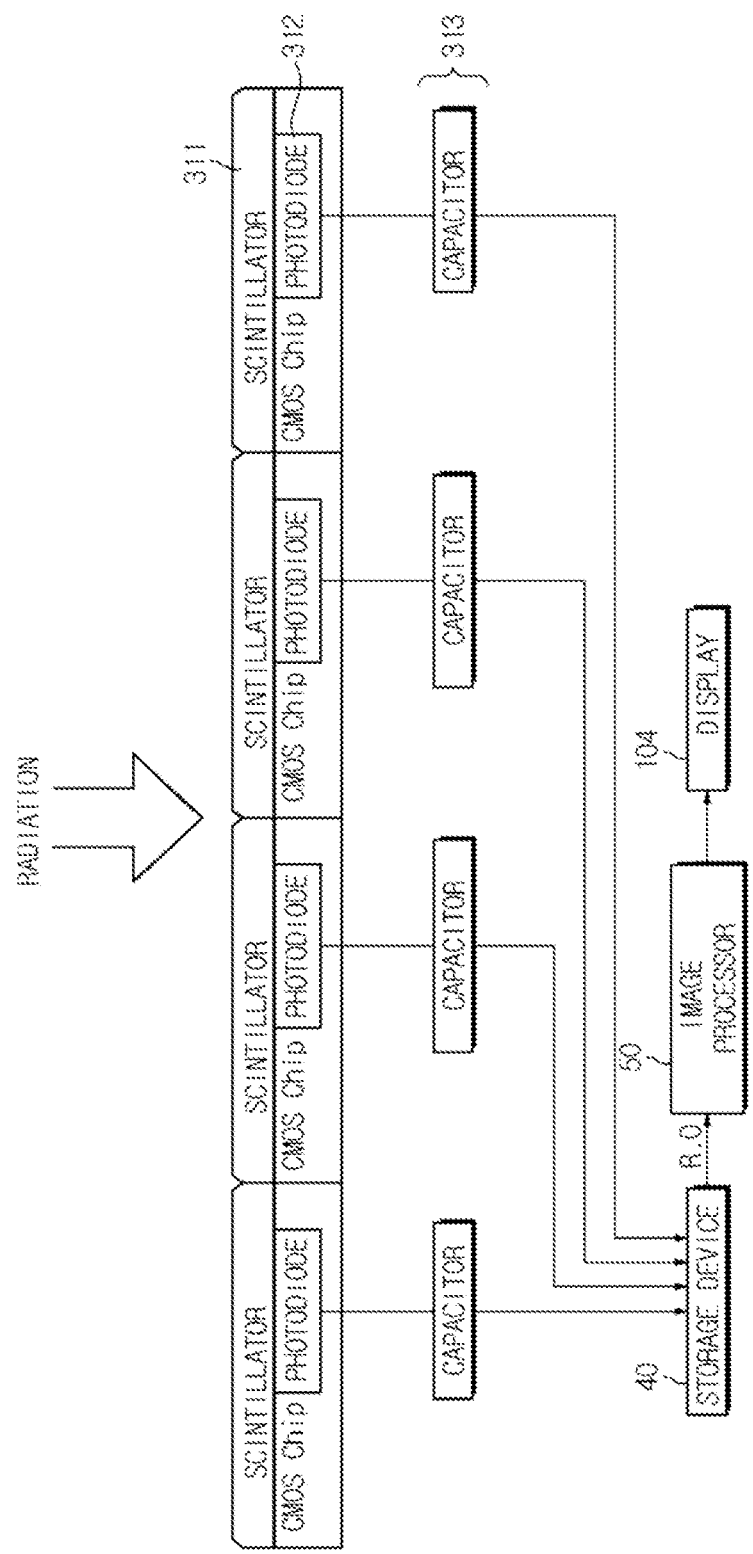
Figure 12:
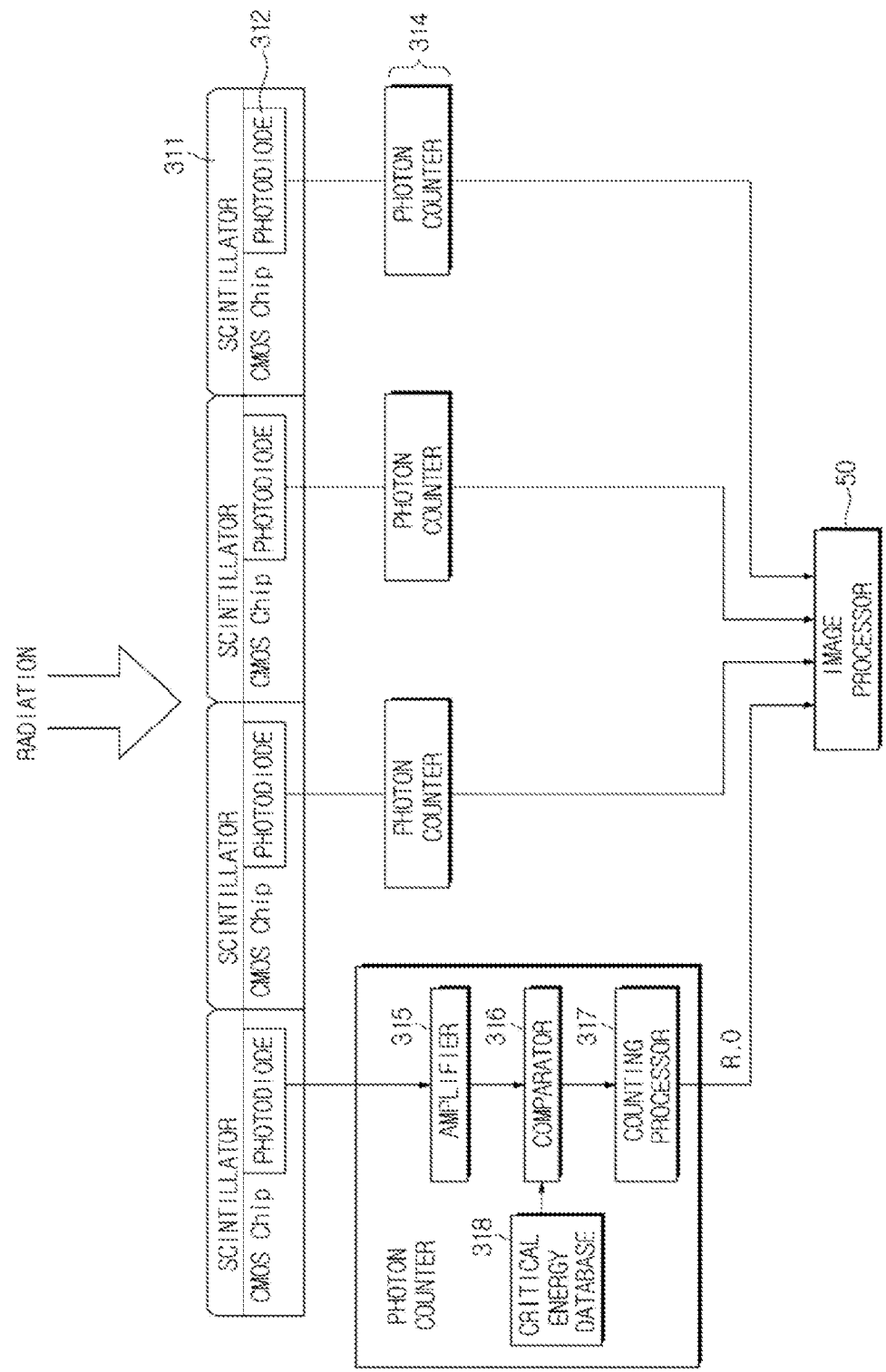

FIGS. 10 to 12 are views of radiation detectors in accordance with an exemplary embodiment.

The radiation detector 30 may convert received radiation directly into an electrical signal (referred to as a direct method), or output visible rays according to received radiation and convert the output visible rays into an electrical signal (referred to as an indirect method).

FIG. 10 illustrates the radiation detector 30 employing the direct method. As exemplarily shown in FIG. 10, the radiation detector 30 of the direct method in accordance with an exemplary embodiment may include a radiation detection panel 310 including a plurality of pixels 310p, and each pixel 310p may include a light receiving element 311, a light sensing element 312, and a storage element 313.

The light receiving element 311 may be a scintillator. The scintillator may receive radiation and output designated photons, for example, visible light photons, according to the received radiation. As exemplarily shown in FIG. 10, the scintillator 311 may be combined with a designated CMOS chip. In accordance with an exemplary embodiment, the scintillator 311 may be disposed on the front surface of a wafer and receive radiation (referred to as a front irradiation method). Further, in accordance with another embodiment, the scintillator 311 may be disposed on the rear surface of a wafer and receive radiation (referred to as a rear irradiation method). In case of the front irradiation method, the front surface of the wafer is used as a light receiving unit to collect light, and in case of the rear irradiation method, the rear surface of the wafer is used as a light receiving unit to collect light.

The light sensing element 312 sensing the photons output from the scintillator 311 and outputting an electrical signal may be installed on the CMOS chip. In accordance with an exemplary embodiment, the light sensing element 312 may be a photodiode.

The electrical signal, i.e., a radiographic signal, output from the photodiode 312 may be stored in the storage element 313. In accordance with an exemplary embodiment, the storage element 313 may be a storage capacitor, as exemplarily shown in FIG. 10. The storage capacitor 313 may temporarily or non-temporarily store the radiographic signal.

In accordance with an exemplary embodiment, the radiographic signals stored in the storage capacitors 313 are read out by the image processor 50, as exemplarily shown in FIG. 10, and the image processor 50 generate a radiographic image using the radiographic signals read out from the capacitors 313. The radiographic image generated by the image processor 50 may be transmitted to the display 104 so as to be displayed to a user.

In accordance with another embodiment, the storage capacitors 313 may transmit the radiographic signals to the storage device 40, as exemplarily shown in FIG. 11.

The storage capacitor 313 may store one electrical signal at a time. Therefore, if a new electrical signal is applied to the storage capacitor 313, the existing electrical signal stored in the storage capacitor 313 may be deleted and then the new electrical signal is stored in the storage capacitor 313. If radiation is emitted plural times, as shown in FIGS. 5, 7, and 8, the radiographic signal stored in the storage capacitor 313 due to earlier emitted radiation may be deleted when new radiation is emitted. Therefore, in order to prevent loss of the radiographic signal due to the earlier emitted radiation, the image processor 50 needs to read out the radiographic signal from the storage capacitor 313 whenever radiation is emitted. If a long time is taken to read out the radiographic signal from the storage capacitor 313, emission of new radiation may be excessively delayed. That is, a time interval between emissions of radiation may be excessively increased. The storage device 40 may separately store the radiographic signal of the storage capacitors 313. Thereby, the image processor 50 may not read out the radiographic signal stored in the storage capacitor 313 whenever radiation is emitted. That is, if radiation is emitted plural times, a radiographic signal acquired whenever radiation is emitted is stored in the separate storage device 40 and thus, the image processor 50 may read out a plurality of radiographic signals, stored in the storage device 40 due to plural emissions of radiation, at once. Therefore, although the image processor 50 does not read out the radiographic signal whenever radiation is emitted, a plurality of radiographic images according to plural emissions of radiation may be acquired.

In accordance with an exemplary embodiment, the above-described storage device 40 may be one of various storage devices which may temporarily or non-temporarily store electrical signals, such as a buffer, a RAM, a magnetic disc, a semiconductor memory device, and an optical memory device.

Further, as exemplarily shown in FIG. 12, the radiation detector 30 may include photon counters 314. The photon counter 314 may count photons output from the photodiode 312 and analyze radiation photons according to energy bands.

Specifically, the photon counter 314 may measure the number of radiation photons exceeding critical energy, output only an electrical signal by only radiation exceeding the critical energy according to a result of measurement, and thus separate the radiation photons according to energy bands.

Each photodiode 312 of each pixel 310p may be connected to each photon counter 314, as exemplarily shown in FIG. 12, and each photon counter 314 connected to each pixel 310p may analyze an electrical signal output from each pixel 310p according to energy bands.

In accordance with an exemplary embodiment, the photon counter 314 may include an amplifier 315, a comparator 316, and a counting processor 317, as exemplarily shown in FIG. 12.

The amplifier 315 may amplify an electrical signal output from the photodiode 132 and output the amplified electrical signal of designated voltage.

The comparator 316 may judge whether or not the electrical signal amplified by the amplifier 315 exceeds or is less than critical energy through comparison, and output a signal according to a result of comparison. In this case, the comparator 316 may judge whether or not the electrical signal exceeds or is less than the critical energy by comparing voltage of the electrical signal with critical voltage corresponding to the critical energy.

The designated critical energy used as a reference of comparison in the comparator 316 may be stored in a separate critical energy database 318. The comparator 316 may read the critical energy database 318, call designated critical energy from the critical energy database 318 according to user selection or system settings, and compare the electrical energy amplified by the amplifier 315 with the called designated critical energy.

In accordance with an exemplary embodiment, the comparator 316 may generate and output a binary signal according to a result of comparison. For example, as a result of comparison between the electrical signal and the critical energy, if the electrical signal is equal to or exceeds the critical energy, the comparator 316 may output a signal having a value of 1, and on the other hand, if the electrical signal is less than the critical energy, the comparator 316 may output a signal having a value of 0. The signal according to the result of comparison, i.e., the binary signal output from the comparator 316, is transmitted to the counting processor 317.

The counting processor 317 may count the number of photons exceeding the critical energy according to the signal transmitted from the comparator 316, and output photon counting result information. The photon counting result information may be used as the intensity of radiation. In accordance with an exemplary embodiment, the counting processor 317 may count photons exceeding the critical energy by counting only the signal having a value of 1 output from the comparator 316.

The intensity of radiation output from the photon counters 314 of the radiation detector 30 may be transmitted to the image processor 50, as exemplarily shown in FIG. 12, and the image processor 50 may generate an image based on the intensity of radiation. In accordance with exemplary embodiments, the intensity of radiation may be stored in the above-described separate storage device 40.

Hereinafter, the image processor 50 will be described.

Figure 13:
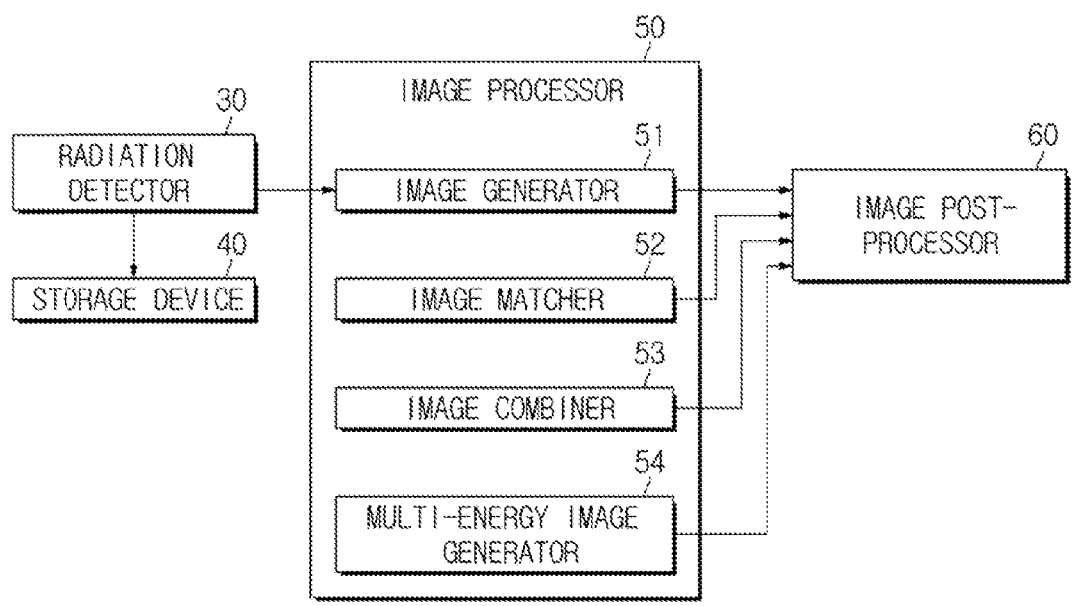
FIG. 13 is a view illustrating the configuration of an image processor in accordance with an exemplary embodiment.

FIG. 13 is a view illustrating the configuration of an image processor in accordance with an exemplary embodiment.

The image processor 50, as exemplarily shown in FIG. 13, may receive a radiographic signal from the radiation detector 30 or the storage device 40, generate a designated radiographic image based on the received radiographic signal, and then output the generated radiographic image.

In accordance with an exemplary embodiment, the image processor 50 may include an image generator 51, an image matcher 52, an image combiner 53, and a multi-energy image generator 54.

The image generator 51 may generate a designated radiographic image based on the received radiographic signal. In this case, the image generator 51 may a separate radiographic image whenever radiation is emitted. In accordance with exemplary embodiments, designated image processing upon the radiographic image generated by the image generator 51 may be carried out.

Figure 14:
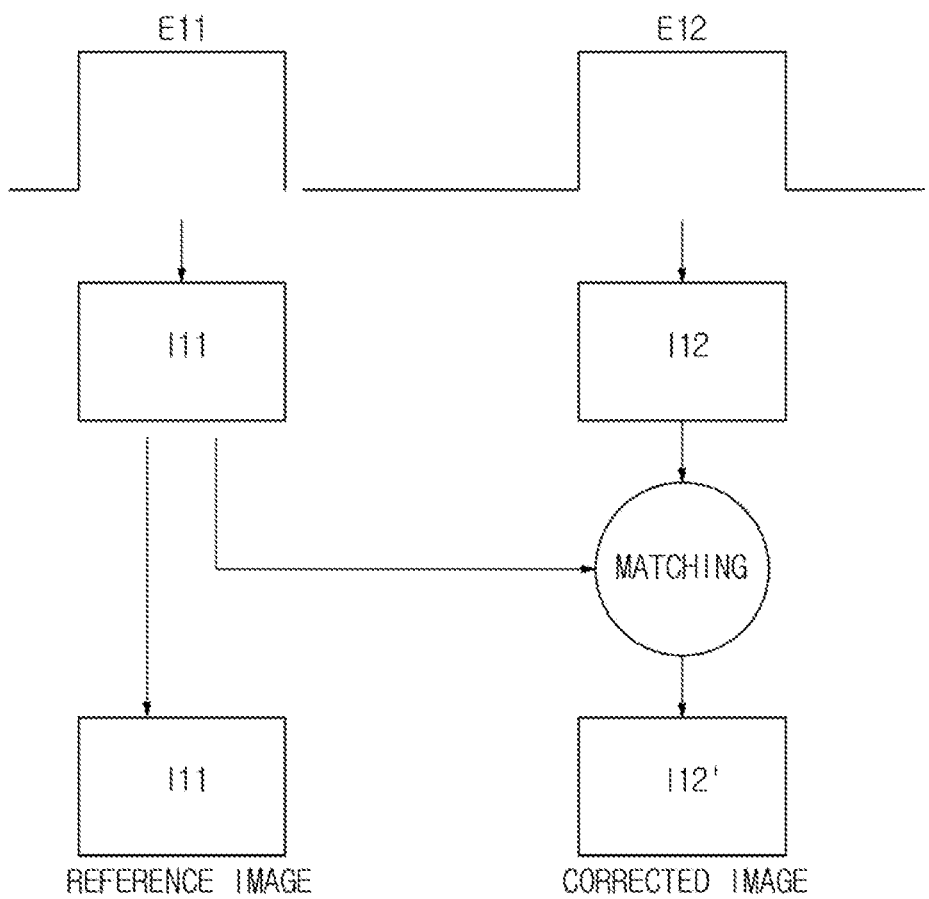
FIGS. 14, 15, and 16 are views illustrating matching methods in accordance with an exemplary embodiment.

FIG. 14 is a view illustrating a matching method in accordance with an exemplary embodiment.

As exemplarily shown in FIG. 14, the image generator 51 may generate an eleventh radiographic image I11 using a radiographic signal according to emission of eleventh radiation, and generate a twelfth radiographic image I12 using a radiographic signal according to emission of twelfth radiation. If the radiation source 20 emits radiation of different energies, as exemplarily shown in FIGS. 7 and 8, the image generator 51 may generate a plurality of radiographic images of different energies corresponding to the number of times of irradiation.

The image matcher 52 matches the plural radiographic images. Matching is an image processing technique in which different images are deformed and displayed as one coordinate system, e.g., the matching of a plurality of images may be performed by correcting at least one of the plurality of images such that each position of an article displayed by each of the plurality of images is equal as a result of the correcting. The image matcher 52 may match plural radiographic images, for example, the eleventh radiographic image I11 and the twelfth radiographic image I12, as exemplarily shown in FIG. 14. In this case, the image matcher 52 may match the plural radiographic images, for example, the eleventh radiographic image I11 and the twelfth radiographic image I12, using one image, for example, the eleventh radiographic image I11, as a reference image.

Further, the image matcher 52 may generate at least one corrected image I12' by correcting at least one radiographic image based on a result of image matching.

Figure 15:
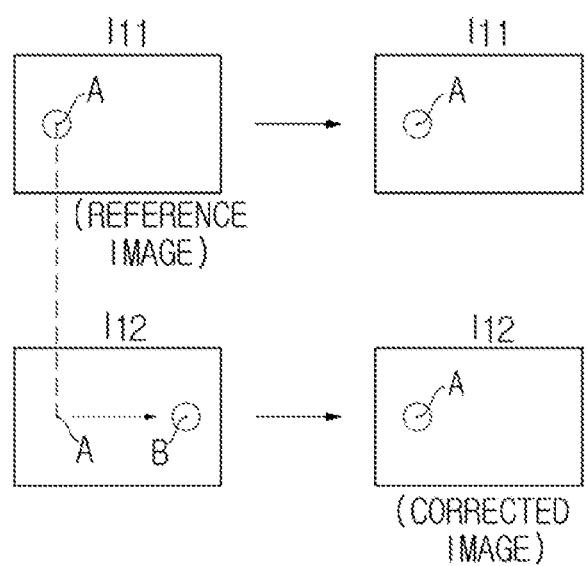
Figure 16:
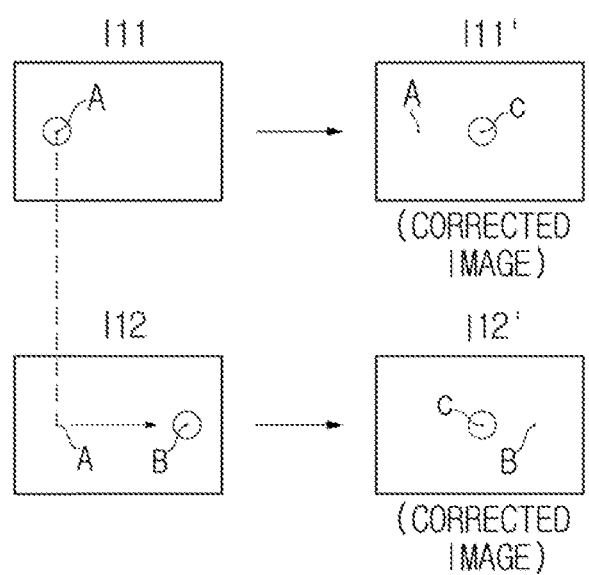

FIGS. 15 and 16 are views illustrating matching methods in accordance with an exemplary embodiment.

As exemplarily shown in FIG. 15, in accordance with an exemplary embodiment, the image matcher 52 may match plural radiographic images, for example, the eleventh radiographic image I11 and the twelfth radiographic image I12. The eleventh radiographic image I11 and the twelfth radiographic image I12 shown at the left of FIG. 15 are radiographic images acquired by imaging the same object 106 at different times. In this case, the eleventh radiographic image I11 and the twelfth radiographic image I12 may be different due to difference of imaging times. That is, a designated article displayed at a specific position A of the eleventh radiographic image I11 may be displayed at a position B of the twelfth radiographic image I12 different from the position A. In this case, the image matcher 52 may match the eleventh radiographic image I11 and the twelfth radiographic image I12 using a designated radiographic image, for example, the eleventh radiographic image I11, as a reference image.

Further, the image matcher 52 may correct at least one radiographic image to be matched according to the reference image. For example, the image matcher 52 may, based on at least one reference image from among the eleventh radiographic image I11 and the twelfth radiographic image I12, for example, the eleventh radiographic image I11, correct another radiographic image, for example, the twelfth radiographic image I12, thus acquiring the eleventh radiographic image I11 and the corrected twelfth radiographic image I12', shown at the right of FIG. 15. In this case, since the eleventh radiographic image I11 is used as the reference image, correction of the eleventh radiographic image I11 may not occur. Further, since the corrected twelfth radiographic image I12' is an image corrected based on the eleventh radiographic image I11 used as the reference image, the corrected twelfth radiographic image I12' may be equal to or almost similar to the eleventh radiographic image I11.

If three or more radiographic images are matched, two radiographic images among the three radiographic images are first matched and at this time, based on one of the two radiographic images as a reference image, another radiographic image may be corrected. Thereby, the reference image and a radiographic image corrected based on the reference image may be acquired. Thereafter, the radiographic image used as the reference image or the corrected radiographic image and the other radiographic image may be matched. In this case, the radiographic image used as the reference image or the corrected radiographic image may be used as a reference image to correct the other radiographic image.

As exemplarily shown in FIG. 16, in accordance with another embodiment, the image matcher 52 may acquire plural radiographic images by correcting plural radiographic images, for example, the eleventh radiographic image I11 and the twelfth radiographic image I12. In the same manner as the embodiment shown in FIG. 15, the eleventh radiographic image I11 and the twelfth radiographic image I12 shown at the left of FIG. 16 are different radiographic images acquired by imaging the same object 106 at different times. In this case, the image matcher 52 may not use a designated radiographic image as a reference image, and may calculate the intermediate value or the mean value of the eleventh radiographic image I11 and the twelfth radiographic image I12 and then first generate a reference image used in matching according to a result of calculation. Thereafter, the image matcher 52 may acquire plural radiographic images shown at the right of FIG. 16, for example, a corrected eleventh radiographic image I11' and a corrected twelfth radiographic image I12', by matching and correcting the eleventh radiographic image I11 and the twelfth radiographic image I12 based on the reference image. In this case, an article displayed at a specific position A of the eleventh radiographic image I11 and an article displayed at a specific position B of the twelfth radiographic image I12 may be displayed at the intermediate position or the mean position C of the newly acquired radiographic images I11' and I12'.

If three or more radiographic images are matched, two radiographic images among the three radiographic images may first be matched and corrected, thus generating a new radiographic image. Then, the new radiographic image and the other radiographic image of the three radiographic images may be matched.

In accordance with an exemplary embodiment, the image matcher 52 may match plural radiographic images by comparing intensities of the plural radiographic images. Further, in accordance with another embodiment, the image matcher 52 may match plural radiographic images by extracting feature points of the plural radiographic images and comparing the extracted feature points.

Designated image processing upon the radiographic images corrected by the image matcher 52 or the reference image may be further carried out, as needed.

The image combiner 53 may generate at least one composite radiographic image by combining plural radiographic images matched by the image matcher 52, for example, the eleventh radiographic image I11 and the corrected twelfth radiographic image I12', as exemplarily shown in FIG. 14.

Since the respective radiographic images, for example, the eleventh radiographic image I11 and the twelfth radiographic image I12, are radiographic images acquired by dividing a radiation exposure dose, as described above, sharpness and accuracy of the respective radiographic images may be lowered as compared to a radiographic image acquired by emitting a radiation exposure dose required to generate a radiographic image one time. When the plural radiographic images acquired according to divided radiation exposure doses are combined, a radiographic image of high quality equal to or similar to the radiographic image acquired by emitting a radiation exposure dose required to generate a radiographic image one time may be acquired.

Further, in accordance with exemplary embodiments, designated image processing upon the composite radiographic image acquired by the image combiner 53 may be carried out.

The multi-energy image generator 54, if plural multi-energy radiographic images are acquired by respectively dividing exposure doses of radiation of plural energies and emitting the radiation of plural energies to the object 106 plural numbers of times corresponding to the numbers of division, as exemplarily shown in FIGS. 7 and 8, generates a multi-energy image using the plurality of multi-energy radiographic images.

Hereinafter, a process of generating a multi-energy image through the multi-energy image generator 54 will be described in detail.

Figure 17:
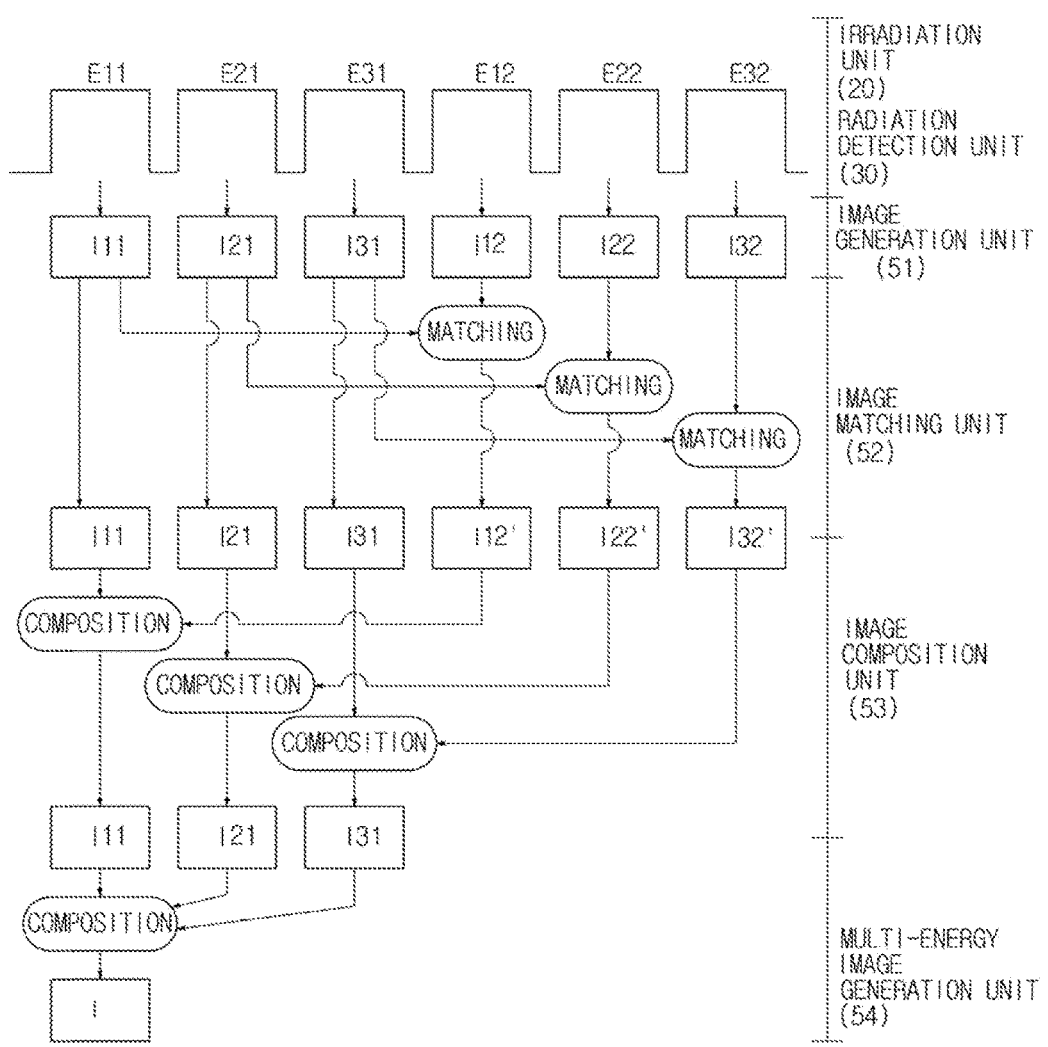
FIG. 17 is a view illustrating a process of generating a multi-energy image.

FIG. 17 is a view illustrating a process of generating a multi-energy image.

As exemplarily shown in FIG. 17, when the radiation source 20 divides exposure doses of radiation E1 to radiation E3 of different energies E1 to E3 into a designated number of radiation dose portions and emits radiation dose portions E11 to radiation E32 to the object 106 the number of times corresponding to the number of radiation dose portions, the radiation detector 30 receives the emitted radiation E11 to radiation E32 and converts the received radiation E11 to radiation E32 into radiographic signals. The image generator 51 of the image processor 50 generates plural radiographic images I11 to I32 corresponding to the number of times of the radiation has been emitted by using the radiographic signals acquired by the radiation detector 30.

The image matcher 52 may match plural radiographic images acquired by emission of radiation of the same energy among the plural radiographic images I11 to I32. For example, the image matcher 52 may match the eleventh radiographic image I11 and the twelfth radiographic image I12, or match the twenty-first radiographic image I21 and the twenty-second radiographic image I22.

In accordance with an exemplary embodiment, plural radiographic images acquired by emitting radiation of the same energy may be matched using one of the plural radiographic images acquired by emitting radiation of the same energy as a reference image. Further, after matching, plural radiographic images may be acquired by correcting radiographic images other than the reference image according to a result of matching, as exemplarily shown in FIG. 17. In this case, the acquired plural radiographic images may be, for example, the plural radiographic images I11, I21, and I31 used as reference images and plural radiographic images I12', I22' and I32' having been matched and corrected based on the reference images.

Of course, matching may be carried out not using at least one radiographic image as a reference image, as exemplarily shown in FIG. 16.

Further, the image matcher 52 may match plural radiographic images acquired by emitting radiation of different energies using one of the plural radiographic images acquired by emitting radiation of different energies as a reference image.

Moreover, the image matcher 52 may match three or more radiographic images. In this case, the three or more radiographic images may be radiographic images acquired by emitting radiation of the same energy, radiographic images acquired by emitting radiation of energies which are partially the same or partially different, or radiographic images acquired by emitting radiation of different energies.

The image combiner 53 may generate composite radiographic images by combining the plural radiographic images. For example, the image combiner 53 may generate at least one radiographic image by combining the at least one radiographic image as the reference and the at least one radiographic image matched and corrected using the reference image, as exemplarily shown in FIG. 17. Further, the image combiner 53 may generate at least one radiographic image by combining the plural radiographic images matched through the method shown in FIG. 16.

In accordance with an exemplary embodiment, the image combiner 53 may generate a composite radiographic image I1 by combining the plural radiographic images acquired by emitting radiation of the same energy, for example, the eleventh radiographic image I11 and the corrected twelfth radiographic image I12', as exemplarily shown in FIG. 17. Of course, the image combiner 53 may combine plural radiographic images acquired by emitting radiation of different energies.

The image combiner 53 may generate at least one multi-energy radiographic image I by overlapping, for example, at least two of the plural radiographic images I11 to I32', for example, the eleventh radiographic image I11 and the twelfth radiographic image I12. In this case, at least one composite radiographic image, for example, the first radiographic image I1, may be acquired by combining the eleventh radiographic image I11 and the twelfth radiographic image I12 by applying or not applying designated weights to the eleventh radiographic image I11 and the twelfth radiographic image I12.

The image combiner 53 may acquire plural composite radiographic images, for example, the first to third radiographic images I1 to I3, as exemplarily shown in FIG. 17, through the above-described method.

The multi-energy image generator 54 may generate at least one multi-energy radiographic image I by combining the plural radiographic images acquired by the image combiner 53. In this case, the plural radiographic combined by the multi-energy image generator 54 may be plural composite radiographic images I1 to I3 acquired by matching and combining the plural radiographic images I11 to I32 acquired by emitting radiation of different energies.

For example, the multi-energy image generator 54 may acquire the at least one multi-energy radiographic image I by overlapping the plural composite radiographic images I1 to I3, or acquire the at least one multi-energy radiographic image I by applying designated weight to at least one of the plural composite radiographic images I1 to I3 a and then combining the images.

The image processor 50 may transmit various kinds of radiographic images, such as the radiographic images generated by the image generator 51, the matched radiographic images acquired by the image matcher 52, the composite radiographic images acquired by the image combiner 53, and the multi-energy radiographic image generated by the multi-energy image generator 54, to an image post-processor 60, as exemplarily shown in FIG. 1. In accordance with exemplary embodiments, the image processor 50 may transmit the radiographic images to a memory device, such as a semiconductor memory device or a magnetic disc memory device, so as to store the radiographic images. Further, the image processor 50 may transmit the radiographic images to the display 104 installed in the radiographic imaging apparatus 1 or a workstation so as to display the radiographic images to a user.

In accordance with an exemplary embodiment, the image post-processor 60 may correct radiographic images by adjusting brightness, contrast, or sharpness of all or a part of radiographic images output from the image processor 50. Further, the image post-processor 60 may perform post-processing of radiographic images by applying various post-processing methods to the radiographic images. Moreover, the image post-processor 60 may generate an overlapping radiographic image by overlapping plural radiographic images, or generate a 3D radiographic image using plural radiographic images. The post-processed radiographic images may be stored in the memory device, such as a semiconductor memory device or a magnetic disc memory device, or be transmitted to the display 104 installed in the radiographic imaging apparatus 1 or the workstation.

According to the above description, if radiographic images or a multi-energy radiographic image is acquired, movement of an object may be compensated for and thus, various problems caused by movement of the object, for example, various noises or artifacts on a radiographic image and distortion among plural radiographic images, may be prevented.

Hereinafter, with reference to FIGS. 18 to 20, a radiographic image generation method will be described.

Figure 18:
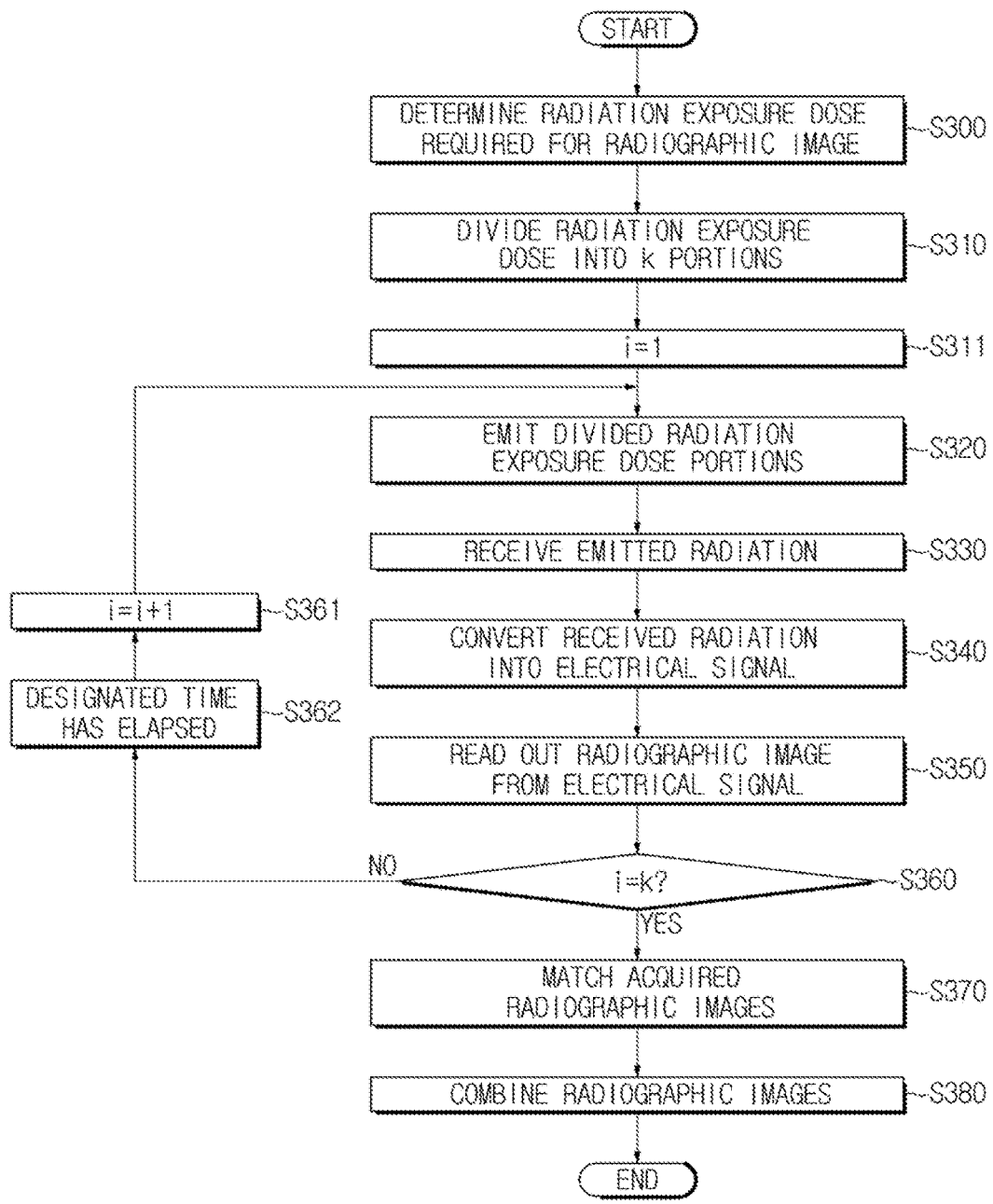
FIGS. 18, 19, and 20 are flowcharts illustrating radiographic image generation methods in accordance with an exemplary embodiment.

FIG. 18 is a flowchart illustrating a radiographic image generation method in accordance with an exemplary embodiment.

As exemplarily shown in FIG. 18, a designated radiation exposure dose required for radiography to generate a radiographic image may be determined (Operation S300).

Thereafter, the radiation exposure dose is divided into a designated number of radiation dose portions, for example, k, according to user selection or system settings (Operation S310). In this case, the radiation exposure dose may be equally divided, but an exemplary embodiment is not limited thereto.

Thereafter, radiation is emitted in a direction of an object 106 (Operations S311 and S320). In this case, the exposure dose of the emitted radiation corresponds to the divided radiation exposure dose. Radiation transmitted by the object 106 or not directly reaching the object 106 is received by the radiation detector (Operation S330). The received radiation is converted into an electrical signal, i.e., a radiographic signal, and the radiographic signal is stored in a designated storage device (Operation S340). Thereafter, a radiographic image is generated by reading out the radiographic signal from the designated storage device (Operation S350).

By repeating the above-described Operation S320 to Operation S350 the number of times corresponding to the number of the radiation exposure dose portions, for example, k times, k radiographic images are acquired (Operations S360 and S361). In this case, emission of (i+1)$^{th}$ radiation may be performed after a designated time from emission of i$^{th}$ radiation has elapsed (Operation S362). Further, the exposure dose of the (i+1)$^{th}$ radiation may be equal to or different from the exposure dose of the i$^{th}$ radiation.

Plural radiographic images acquired through the above-described process, for example, k radiographic images, are matched (Operation S370). In this case, image matching may be performed upon some of the plural radiographic images or all of the plural radiographic images. Further, in order to match the radiographic images, at least one of the plural radiographic images may be used as a reference image. As needed, some radiographic images may be corrected based on a result of matching. In this case, corrected radiographic images may be images other than the reference image.

When the plural radiographic images are matched, a composite radiographic image is acquired by combining the plural radiographic images according to a result of matching (Operation S380). Here, the composite radiographic image may be acquired by combining the reference image and the image corrected according to the result of matching or combining the images corrected according to the result of matching.

Thereby, a radiographic image, in which movement of an object, for example, a patient, has been compensated for, may be acquired.

Figure 19:
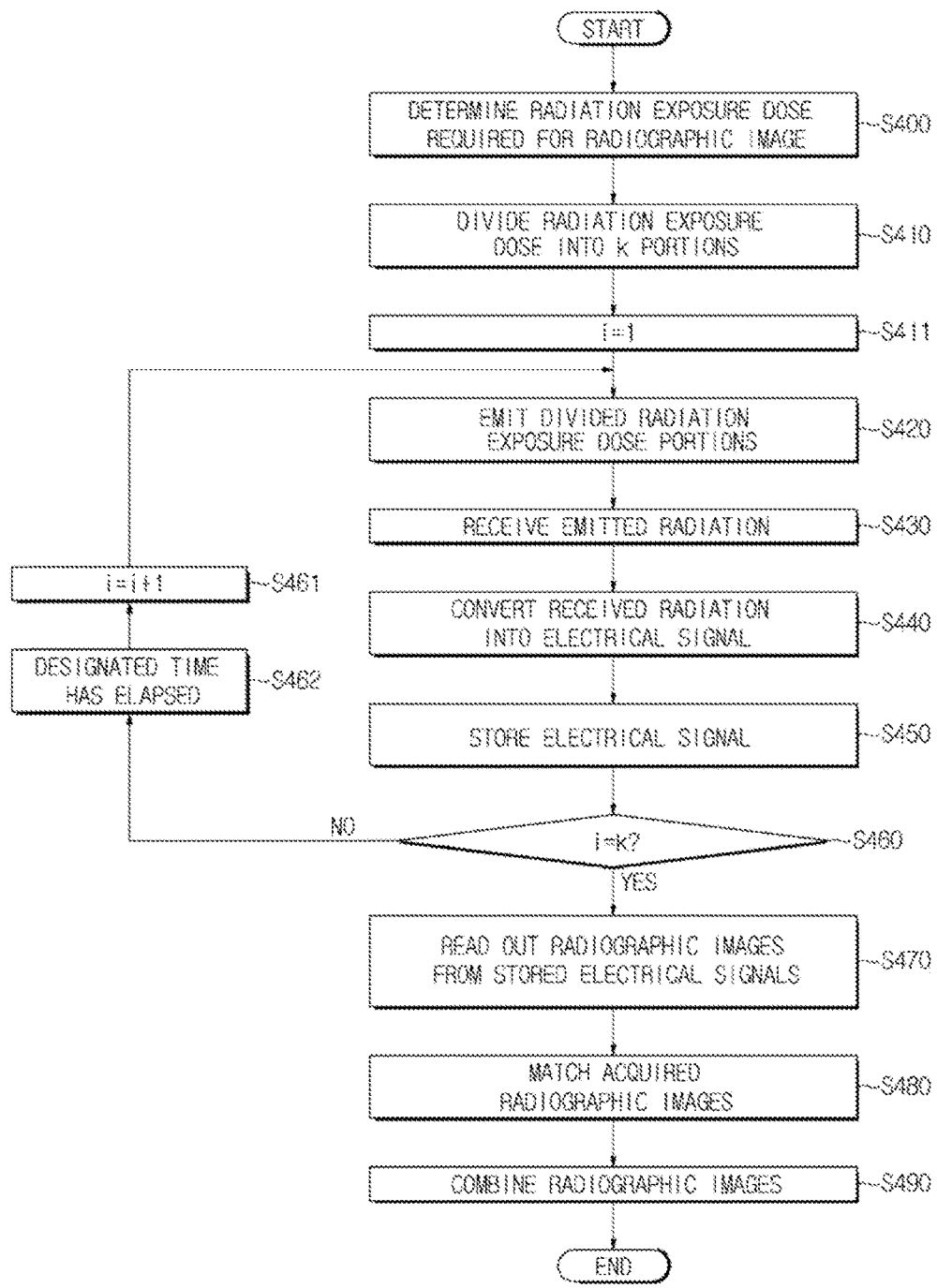

FIG. 19 is a flowchart illustrating a radiographic image generation method in accordance with another embodiment.

As exemplarily shown in FIG. 19, in the radiographic image generation method in accordance with an exemplary embodiment, a designated radiation exposure dose required to generate a radiographic image may be determined (Operation S400). The radiation exposure dose is divided into a designated number of radiation dose portions, for example, k, according to user selection or system settings (Operation S410) and an index i which corresponds to the number of radiations is initialized by setting i=1 in Operation S411. In the same manner as the earlier embodiment of FIG. 18, the radiation exposure dose may be equally divided, but an exemplary embodiment is not limited thereto. That is, divided radiation exposure doses may be different.

Thereafter, radiation is emitted according to the divided radiation exposure dose (Operation S420), the emitted radiation is received (Operation S430), and the received radiation is converted into a designated electrical signal, i.e., a radiographic signal (Operation S440).

Thereafter, the acquired radiographic signal is stored in a designated storage device (Operation S450). In this case, the storage device may temporarily or non-temporarily store the radiographic signal. Further, the storage device may store all of radiographic signals acquired through plural emission of radiation.

By repeating the above-described Operation S420 to Operation S450 the number of times corresponding to the number of the radiation exposure dose portions, for example, k times, plural radiographic signals with respect to k radiographic images are acquired (Operations S460 and S461). In this case, emission of (i+1)$^{th}$ radiation may be performed after a designated time from emission of i$^{th}$ radiation has elapsed (Operation S462). Further, the exposure dose of the (i+1)$^{th}$ radiation may be equal to or different from the exposure dose of the i$^{th}$ radiation.

When emission of radiation has been completed, when radiation has emitted the number of times of irradiation stored in advance, or according to instructions or a command input by a user, plural radiographic images are generated by reading out plural radiographic signals stored in the above-described storage device through the image processor (Operation S470). Consequently, the plural radiographic images are acquired.

The acquired plural radiographic images, for example, k radiographic images, are matched (Operation S480). In the same manner as the earlier embodiment of FIG. 18, image matching may be performed upon some of the plural radiographic images or all of the plural radiographic images. Further, in order to match the radiographic images, at least one of the plural radiographic images may be used as a reference image. As needed, some radiographic images may be corrected based on a result of matching. In this case, corrected radiographic images may be images other than the reference image.

When the plural radiographic images are matched, a composite radiographic image is acquired by combining the plural radiographic images according to a result of matching (Operation S490). Here, the composite radiographic image may be acquired by combining the reference image and the image corrected according to the result of matching or combining the images corrected according to the result of matching.

Thereby, delay of a radiographic imaging time due to readout of a radiographic signal may be prevented.

Figure 20:
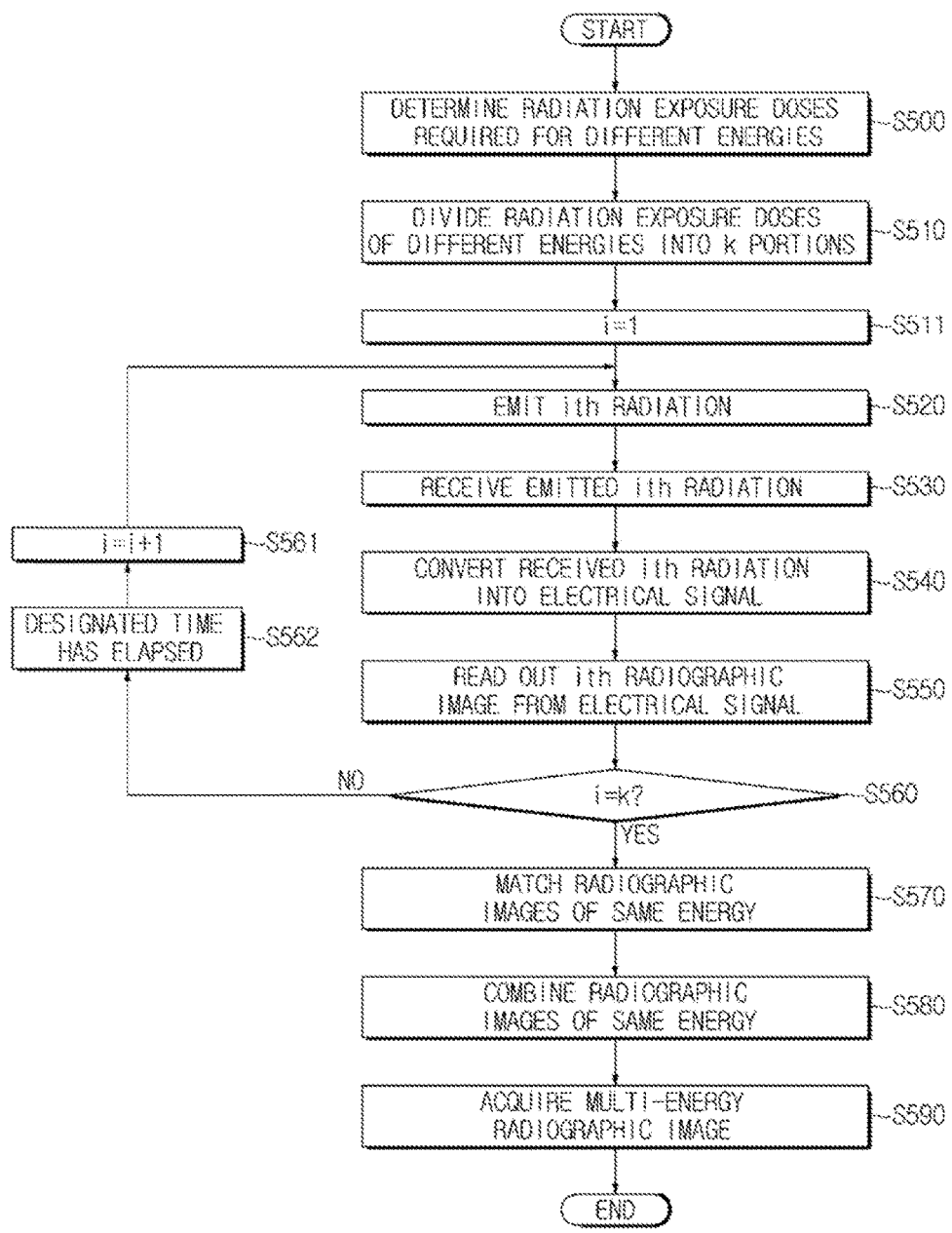

FIG. 20 is a flowchart illustrating a multi-energy radiographic image generation method in accordance with an exemplary embodiment.

As exemplarily shown in FIG. 20, in the multi-energy radiographic image generation method in accordance with an exemplary embodiment, exposure doses of plural radiations to be emitted to an object to acquire a multi-energy radiographic image may first be determined (Operation S500). In this case, the respective plural radiations are radiations of different energies. That is, radiation exposure doses required for the respective different energies may be determined.

Each of the plural radiation exposure doses of different energies is divided into a designated number of radiation dose portions, for example, k, according to user selection or system settings (Operation S510). Here, the plural radiation exposure doses of different energies are divided into the same number of radiation dose portions. Of course, an exemplary embodiment is not limited thereto. A division method may be arbitrarily selected by a user or a system designer. For example, as exemplarily shown in FIG. 8, the radiation exposure doses of radiation of first energy and radiation of second energy may be respectively divided into three and the exposure dose of radiation of third energy may be divided into six, and thereby, radiation of plural different energies may be totally divided into twelve (in this case, k=12).

Thereafter, the radiation of plural different energies, the exposure doses of which have been divided, may be emitted to an object according to a designated pattern. In this case, the designated pattern may be defined, as exemplarily shown in FIG. 7 or 8, or be arbitrarily defined by the user or the system designer (Operations S511, S520, and S560).

Further, whenever radiation is emitted, the emitted radiation may be received (Operation S530), and be converted into an electrical signal, i.e., a radiographic signal (Operation S540). Then, at least one radiographic image may be generated by reading out the converted radiographic signal (Operation S550). Then, by repeating the above-described Operation S520 to Operation S550 the number of times corresponding to the number of the radiation exposure dose portions, for example, k times, plural radiographic signals with respect to k radiographic images are acquired (Operations S560 and S561). In this case, emission of $(i+1)^{th}$ radiation may be performed after a designated time from emission of $i^{th}$ radiation has elapsed (Operation S562). In this case, in accordance with an exemplary embodiment, before a radiographic image is read out, the radiographic signal is separately stored in a designated storage space which may store plural radiographic signals and then, at least one radiographic image may be acquired by reading out the radiographic signal stored in the designated storage space.

When plural radiographic images are acquired, the plural radiographic images are matched (Operation S570). In accordance with an exemplary embodiment, plural radiographic images of the same energy may be matched. In this case, plural radiographic images may be acquired by correcting a designated radiographic image according to a result of matching. In this case, at least one of the plural radiographic images may be a radiographic image used as a reference image.

When the plural radiographic images are matched, plural radiographic images are combined according to the result of matching (Operation S580). In accordance with an exemplary embodiment, plural composite radiographic images may be acquired by combining plural radiographic images of the same energy.

Thereafter, a multi-energy radiographic image is acquired by combining the plural composite radiographic images acquired through emission the radiation of different energies, image matching, and image combination (Operation S590).

Thereby, a multi-energy radiographic image, in which movement of an object, for example, a human body, due to exposure for a long time has been compensated for, may be acquired.

As is apparent from the above description, a radiographic imaging apparatus and a radiographic image generation method in accordance with an exemplary embodiment may acquire a radiographic image in which movement of an object has been compensated for, in case of acquisition of at least one radiographic image.

Therefore, degradation of the radiographic image due to movement of the object may be prevented, and a radiographic image, from which various problems, for example, noise and artifacts, are removed or minimized, may be acquired.

Further, in case of acquisition of plural radiographic images, difference among the plural radiographic images caused by image shaking due to movement of the object may be prevented or corrected.

Moreover, in case of acquisition of the multi-energy radiographic image, various problems generated according to difference among plural radiographic images acquired by emitting radiation of plural different energies may be effectively prevented.

Further, in case of acquisition of the multi-energy radiographic image, a clear multi-energy radiographic image without quality degradation may be acquired by removing difference among plural radiographic images due to movement of the object.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A radiographic image generation method comprising:
dividing a first radiation exposure dose of a first energy to be emitted to an object into a plurality of first radiation dose portions and dividing a second radiation exposure dose of a second energy into a plurality of second radiation dose portions;
emitting the plurality of first radiation dose portions and the plurality of second radiation dose portions to the object a number of times corresponding to a number of the plurality of first radiation dose portions and a number of the plurality of second radiation dose portions with varying an irradiation time of each radiation dose portion;
acquiring a plurality of radiographic images corresponding to the plurality of first radiation dose portions and the plurality of second radiation dose portions by detecting the plurality of first radiation dose portions and the plurality of second radiation dose portions that have been passed through the object; and
aligning the acquired plurality of radiographic images by correcting a position of at least one of the acquired plurality of radiographic images such that an image region of an article displayed by each of the plurality of radiographic images is positioned at a same relative position in each of the plurality of radiographic images as a result of the correcting.

2. The radiographic image generation method according to claim 1, wherein the acquiring the plurality of radiographic images comprises:
acquiring the plurality of radiographic images by emitting the plurality of first radiation dose portions and the plurality of second radiation dose portions to the object at regular time intervals.

3. The radiographic image generation method according to claim 1, further comprising:
emitting the plurality of first radiation dose portions and the plurality of second radiation dose portions to the object according to a pattern.

4. The radiographic image generation method according to claim 1, further comprising:
emitting the plurality of first radiation dose portions and the plurality of second radiation dose portions to the object sequentially.

5. The radiographic image generation method according to claim 1, wherein the acquiring the plurality of radiographic images comprises:
acquiring the plurality of radiographic images by repeatedly emitting radiation to the object according to the divided plurality of first radiation dose portions and the plurality of second radiation dose portions;
receiving the radiation;
converting the received radiation into electrical signals;
storing the electrical signals; and
generating a radiographic image from the stored electrical signals.

6. The radiographic image generation method according to claim 1, wherein the acquiring the plurality of radiographic images comprises:
acquiring electrical signals by repeatedly emitting radiation to the object according to the divided plurality of first radiation dose portions, receiving the plurality of first radiation dose portions and the plurality of second radiation dose portions, converting the received radiation into electrical signals and storing the converted electrical signals in a storage device; and acquiring the plurality of radiographic images by generating the plurality of radiographic images from the converted electrical signals.

7. The radiographic image generation method according to claim 1, wherein aligning the acquired plurality of radiographic images comprises:

aligning the plurality of radiographic images acquired by emitting radiation dose portions of a same energy.

8. The radiographic image generation method according to claim 1, further comprising combining the aligned plurality of radiographic images.

9. The radiographic image generation method according to claim 1, further comprising:

generating a multi-energy radiographic image by combining the plurality of radiographic images acquired by emitting the plurality of first radiation dose portions and the plurality of second radiation dose portions.

10. A radiographic imaging apparatus comprising:

a radiation source configured to emit radiation to an object by dividing a first radiation exposure dose of a first energy and a second radiation exposure dose of a second energy, for acquiring a plurality of radiographic images, into a plurality of first radiation dose portions and a plurality of second radiation dose portions respectively, the radiation being emitted to the object a number of times corresponding to a number of the plurality of first radiation dose portions and a number of the plurality of second radiation dose portions with varying an irradiation time of each radiation dose portion;

a radiation detector configured to receive the radiation, convert the received radiation into electrical signals, and output the electrical signals; and an image processor configured to acquire radiographic images corresponding to the number of the plurality of first radiation dose portions and the number of the plurality of second radiation dose portions by reading out the electrical signals, and to align the acquired radiographic images by correcting a position of at least one of the acquired radiographic images such that an image region of an article displayed by each of the radiographic images is positioned at a same relative position in each of the radiographic images as a result of the correcting.

11. The radiographic imaging apparatus according to claim 10, wherein the radiation source is further configured to emit the plurality of first radiation dose portions and the plurality of second radiation dose portions at regular time intervals.

12. The radiographic imaging apparatus according to claim 10, wherein the radiation source is further configured to emit the plurality of first radiation dose portions and the plurality of second radiation dose portion according to a pattern.

13. The radiographic imaging apparatus according to claim 10, further comprising:

a storage device configured to store the electrical signals converted by the radiation detector, temporarily or permanently.

14. The radiographic imaging apparatus according to claim 13, wherein the storage device is further configured to store the electrical signals output at different times.

15. The radiographic imaging apparatus according to claim 14, wherein the image processor is further configured to acquire the plurality of radiographic images by reading out the electrical signals output at the different times, from the storage device.

16. The radiographic imaging apparatus according to claim 10, wherein the image processor is further configured to read out the electrical signals whenever the electrical signals are acquired.

17. The radiographic imaging apparatus according to claim 10, wherein the image processor is further configured to align the plurality of radiographic images acquired by emitting the radiation of a same energy.

18. The radiographic imaging apparatus according to claim 10, wherein the image processor is further configured to combine the plurality of radiographic images which have been aligned.

* * * * *